(12) United States Patent
Shirasaki et al.

(10) Patent No.: US 9,060,694 B2
(45) Date of Patent: Jun. 23, 2015

(54) BLOOD PRESSURE MEASUREMENT DEVICE FOR MEASURING AT APPROPRIATE TIMING

(75) Inventors: Osamu Shirasaki, Amagasaki (JP);
Takashi Watanabe, Kyoto (JP);
Kazuomi Kario, Shimotsuke (JP)

(73) Assignees: OMRON HEALTHCARE Co., Ltd.,
Kyoto (JP); JICHI MEDICAL UNIVERSITY, Tochigi (JP)

( * ) Notice: Subject to any disclaimer, the term of this patent is extended or adjusted under 35 U.S.C. 154(b) by 678 days.

(21) Appl. No.: 12/671,720

(22) PCT Filed: Aug. 5, 2008

(86) PCT No.: PCT/JP2008/064005
§ 371 (c)(1),
(2), (4) Date: Feb. 2, 2010

(87) PCT Pub. No.: WO2009/020114
PCT Pub. Date: Feb. 12, 2009

(65) Prior Publication Data
US 2011/0230729 A1      Sep. 22, 2011

(30) Foreign Application Priority Data

Aug. 9, 2007    (JP) ................................. 2007-208346

(51) Int. Cl.
*A61B 5/0205* (2006.01)
*A61B 5/021* (2006.01)
(Continued)

(52) U.S. Cl.
CPC ............... *A61B 5/0205* (2013.01); *A61B 5/021* (2013.01); *A61B 5/02116* (2013.01); *A61B 5/022* (2013.01);
(Continued)

(58) Field of Classification Search
CPC .... A61B 5/021; A61B 5/022; A61B 5/02208; A61B 5/02216; A61B 5/02225; A61B 5/02233; A61B 5/02241; A61B 5/0225; A61B 5/02255; A61B 5/023; A61B 5/0235; A61B 5/0205

USPC .................................................. 600/485–503
See application file for complete search history.

(56) References Cited

U.S. PATENT DOCUMENTS

| 4,566,463 | A | * | 1/1986 | Taniguchi et al. | 600/495 |
| 4,780,824 | A | * | 10/1988 | Niwa et al. | 600/513 |
| 5,215,096 | A | * | 6/1993 | Zapf et al. | 600/495 |
| 5,785,659 | A | * | 7/1998 | Caro et al. | 600/485 |
| 5,833,619 | A | * | 11/1998 | Freed et al. | 600/485 |

(Continued)

FOREIGN PATENT DOCUMENTS

| EP | 0445809 A2 * | 9/1991 |
| EP | 0875200 A1 * | 11/1998 |

(Continued)

OTHER PUBLICATIONS

International Search Report w/translation from PCT/JP2008/064005 dated Sep. 9, 2008 (4 pages).

*Primary Examiner* — Navin Natnithithadha
*Assistant Examiner* — Meredith Weare
(74) *Attorney, Agent, or Firm* — Osha Liang LLP

(57) ABSTRACT

A blood pressure measurement device includes a finger cuff for measuring a blood oxygen saturation level of a subject as physiological information excluding a blood pressure, a pulse wave detecting portion, and an oxygen saturation level calculating portion, where a start of blood pressure measurement in a sphygmomanometer is determined by a comparing and determining portion when a value becomes greater than or equal to a reference value. After the end of the measurement, a time limit for limiting the start of the blood pressure measurement is set. The comparing and determining portion determines not to start the blood pressure measurement within the time limit even if the blood oxygen saturation level becomes greater than or equal to the reference value.

7 Claims, 19 Drawing Sheets

(51) Int. Cl.
  *A61B 5/1455* (2006.01)
  *A61B 5/022* (2006.01)
  *A61B 5/024* (2006.01)
  *A61B 5/0402* (2006.01)
  *A61B 5/087* (2006.01)
  *A61B 5/00* (2006.01)

(52) U.S. Cl.
  CPC ........... *A61B 5/02422* (2013.01); *A61B 5/0402* (2013.01); *A61B 5/087* (2013.01); *A61B 5/14551* (2013.01); *A61B 5/6824* (2013.01); *A61B 5/6826* (2013.01); *A61B 5/6838* (2013.01)

(56) References Cited

U.S. PATENT DOCUMENTS

| 6,050,951 | A  | * | 4/2000 | Friedman et al. | 600/485 |
| 6,241,680 | B1 | * | 6/2001 | Miwa | 600/494 |
| 2005/0148885 | A1 | * | 7/2005 | Tweed et al. | 600/490 |
| 2005/0187480 | A1 | * | 8/2005 | Kario et al. | 600/483 |

FOREIGN PATENT DOCUMENTS

| EP | 1127538 A1 * | 8/2001 |
| JP | 62-150814 U | 7/1987 |
| JP | 62-155829 A | 7/1987 |
| JP | 9-220205 | 8/1997 |

* cited by examiner

BLOOD PRESSURE MEASUREMENT DEVICE FOR MEASURING AT APPROPRIATE TIMING

TECHNICAL FIELD

The present invention relates to blood pressure measurement devices, in particular, to a blood pressure measurement device for determining a timing of blood pressure measurement.

BACKGROUND ART

For early detection and blood pressure management of lifestyle related diseases caused by hypertension, a sphygmomanometer is being widely used. In recent years, new clinical states of the hypertension have become apparent with the wide spread use of the sphygmomanometer.

For example, a clinical state of morning hypertension shows a daily fluctuation pattern where a blood pressure is usually normal but is specifically high for one to two hours after waking up, and is known to become a strong risk factor of brain and cardiac disease through research. A clinical state of nocturnal hypertension shows a pattern where the blood pressure does not lower or the blood pressure rises during sleep compared to the daytime, and is known to become a strong risk factor of brain and cardiac disease and is deeply related to a sudden death.

Furthermore, the nocturnal hypertension is known to be strongly associated with a sleep apnea syndrome in which breathing stops during sleep. When breathing stops during sleep, a sympathetic nerve activity is increased by hypoxemia or an arousal reaction, and the blood pressure becomes high at night. Thus, measuring the blood pressure during sleep is effective in diagnosis and treatment of hypertension.

As a method of measuring the blood pressure during sleep, there is adopted a method of monitoring a value of an oxygen saturation level, and selectively activating the blood pressure measurement when the value satisfies a predetermined condition, and a method of selectively activating the blood pressure measurement when satisfying a predetermined lowering condition by apnea disclosed in, for example, Japanese Unexamined Patent Publication No. 62-155829 (hereinafter referred to as Patent Document 1). The blood pressure at the time of a physiologic change such as hypoxia can thus be grasped and comparison can be made with the blood pressure at normal time.

[Patent Document 1] Japanese Unexamined Patent Publication No. 62-155829

DISCLOSURE OF THE INVENTION

Problems to be Solved by the Invention

However, the following problems arise when the method disclosed in Patent Document 1 is adopted.

The first problem is that when measurement is carried out for a few hours during sleep, the blood pressure measurement is repeated endlessly if a temporary physiologic change is repeated a number of times, which may give a physical pain and a psychological pain caused by the blood pressure measurement to a subject. Furthermore, a problem in that the measurement may inhibit the sleep of the subject arises.

With respect to the first problem, consideration is made in prohibiting the blood pressure measurement from being repeated endlessly even if a temporary physiologic change satisfying a predetermined reference repeatedly occurs. However, there arises a second problem in that the blood pressure measurement upon indication of the important physiologic change may be inhibited by such a prohibiting configuration. Thus, the true blood pressure state of the subject cannot be captured, which may lead to a false diagnosis, although capturing the blood pressure that became the highest in one night is medically important.

In view of the above problems, it is an object of the present invention to provide a blood pressure measurement device capable of measuring the blood pressure particularly when an important physiologic change occurs without endlessly repeating the blood pressure measurement based on the physiologic change.

Means for Solving the Problems

In order to achieve the above-described object, in accordance with one aspect of the present invention, a blood pressure measurement device includes: a blood pressure measuring portion for measuring a blood pressure of a subject; an acquiring portion for obtaining physiological information on a type excluding the blood pressure of the subject; and a control portion for outputting a control signal for activating the blood pressure measuring portion when the physiological information satisfies a predetermined condition, and setting a time limit for limiting the activation of the blood pressure measuring portion for a predetermined time after the measurement.

In accordance with another aspect of the present invention, a blood pressure measurement includes: a blood pressure measuring portion for measuring a blood pressure of a subject; an acquiring portion for obtaining physiological information on a type excluding the blood pressure of the subject; and a determining portion for determining a start of the measurement in the blood pressure measuring portion and a start of a time limit for limiting the start of the measurement based on the physiological information, and outputting a control signal for activating the blood pressure measuring portion; wherein the determining portion determines to start the measurement when a value obtained from the physiological information satisfies a first condition outside the time limit, and to start the time limit from an end of the measurement, and determines not to start the measurement when the value obtained from the physiological information satisfies the first condition within the time limit.

Effects of the Invention

Through the use of the blood pressure measurement device of the present invention, blood pressure measurement based on a physiological change is not repeated endlessly. Further, the blood pressure can be measured when a particularly important physiological change occurs.

Figure 1:
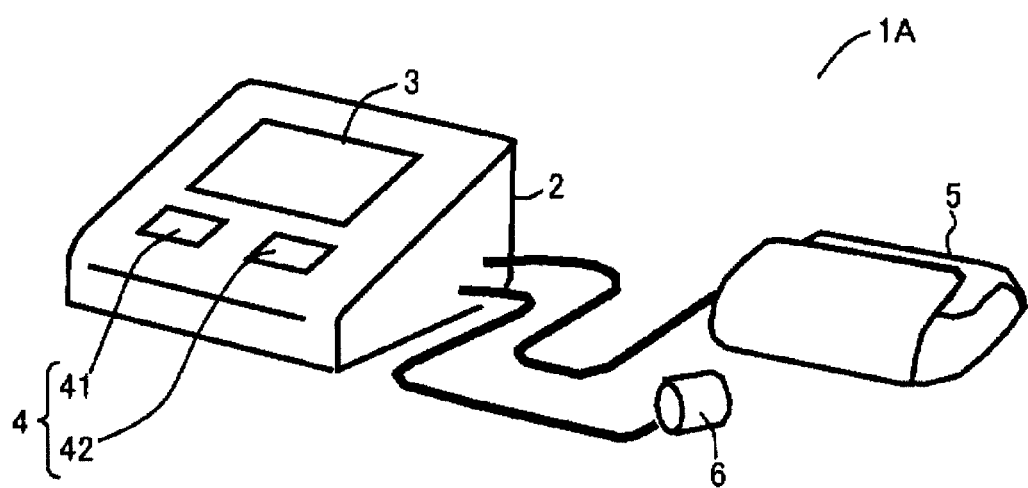
FIG. 1 is a diagram showing a specific example of an outer appearance of a blood pressure measurement device according to a first embodiment.

DESCRIPTION OF THE REFERENCE NUMERALS 1A to 1D blood pressure measurement device
2 housing
3 display unit
4 operation unit
5 upper arm cuff
6 finger cuff
7 CPU
8 sphygmomanometer
9 timing unit
10 processing unit
11 blood pressure storage portion
13 pulse wave detecting portion
14A oxygen saturation level calculating portion
14B heart rate calculating portion
15 comparing and determining portion
20 sensor
21 breathing waveform detecting portion
22 apnea time calculating portion
30 cardiograph sensor
31 cardiograph waveform detecting portion
32 heart rate calculating portion
41 power switch
42 measurement start switch
67 cuff
65 light emitting element
66 light receiving element
151 reference value storage part
152 first comparing part
153 lowest value storage part
154 second comparing part
155 determining part
156 timer
161 calculating part
162 third comparing part
163 update part

BEST MODE FOR CARRYING OUT THE INVENTION

The embodiments of the present invention will be described with reference to the drawings. In the following description, same reference numerals are denoted for the same parts and components. Names and functions thereof are also the same.

First Embodiment

A blood pressure measurement device 1A according to a first embodiment determines a measurement start timing based on a change in oxygen saturation level in blood, which is one type of continuous physiological information excluding a blood pressure, and starts measurement.

Having the blood oxygen saturation level as an index for timing the blood pressure measurement start timing has the following significance. That is, lowering of the oxygen saturation level occurs by respiratory arrest or infrequent respiration during sleep apnea and the like. As the blood pressure level rapidly rises after the apnea attack, a new blood pressure index leading to a prediction of a cardiovascular risk can be obtained by specifying and measuring the blood pressure level at the relevant point.

With reference to FIG. 1, the blood pressure measurement device 1A includes a housing 2, and an upper arm cuff 5 to be wrapped around an upper arm of a subject at the time of blood pressure measurement and a finger cuff 6, which are connected to the housing 2, where a display unit 3 for displaying various types of information including measurement results and an operation unit 4 operated to give various instructions to the blood pressure measurement device 1A are arranged at the front of the housing 2. The operation unit 4 includes a power switch 41 operated to turn ON/OFF a power supply with respect to the blood pressure measurement device 1A, and a measurement start switch 42 operated to give an instruction to start the measurement.

Figure 2:
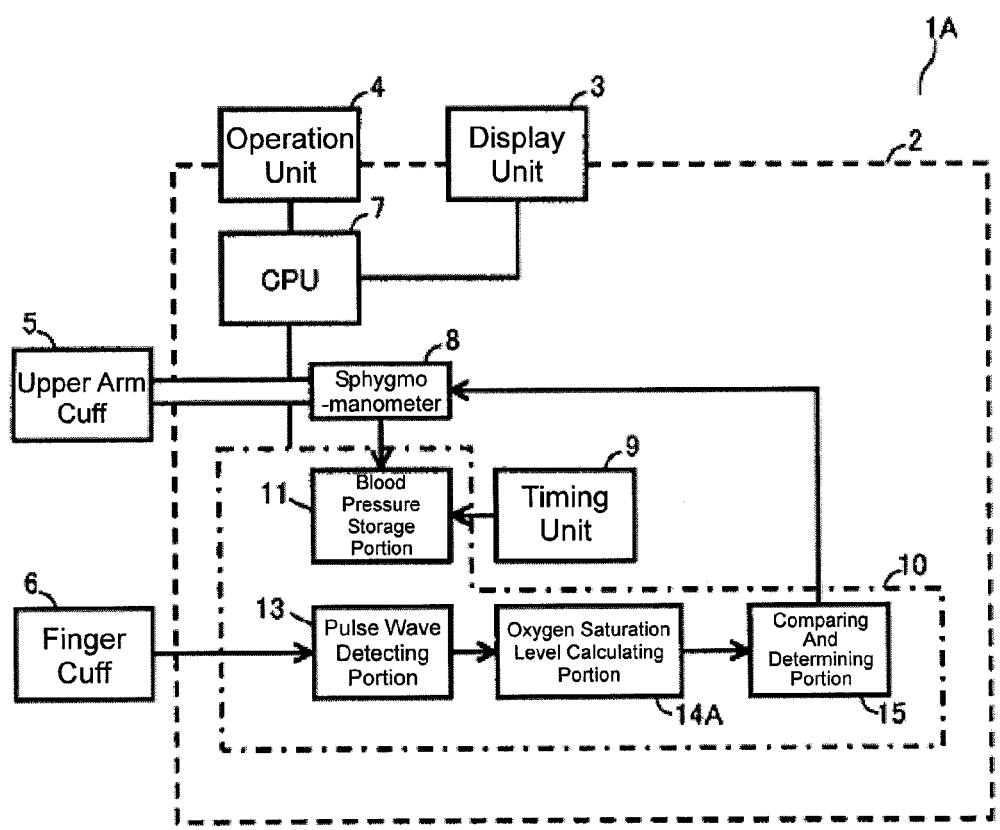
FIG. 2 is a block diagram showing a specific example of a configuration of the blood pressure measurement device according to the first embodiment.

With reference to FIG. 2, a CPU (Central Processing Unit) 7, a sphygmomanometer 8, a timing unit 9 for timing time and outputting time information such as date and time, and time of day, and a processing unit 10 are arranged in the housing 2 of the blood pressure measurement device 1A.

The processing unit 10 includes a blood pressure storage portion 11, a pulse wave detecting portion 13, an oxygen saturation level calculating portion 14A, and a comparing and determining portion 15. The blood pressure storage portion 11 is configured by a memory (not shown), and the pulse wave detecting portion 13, the oxygen saturation level calculating portion 14A and the comparing and determining portion 15 are provided as a program. The program is stored in a memory (not shown). The CPU 7 controls the access with respect to the blood pressure storage portion 11, and controls the execution of the program of the pulse wave detecting portion 13 and the oxygen saturation level calculating portion 14A.

The sphygmomanometer 8 is connected with the upper arm cuff 5 with an air tube to measure the blood pressure based on a pressure signal detected from the upper arm cuff 5 and output a blood pressure value, according to an activation signal from the comparing and determining portion 15 described below. The sphygmomanometer 8 and the upper arm cuff 5 have the well-known configuration. Every time the blood pressure value is inputted from the sphygmomanometer 8, the blood pressure storage portion 11 stores the same in association with the time information outputted from the timing unit 9. The upper arm cuff 5, the sphygmomanometer 8, the timing unit 9, and the blood pressure storage portion 11 configure a blood pressure measurement system. The content of the blood pressure storage portion 11 is read out according to the operation signal corresponding to the operation of the operation unit 4 by a user, and displayed on the display unit 3.

Figure 3:
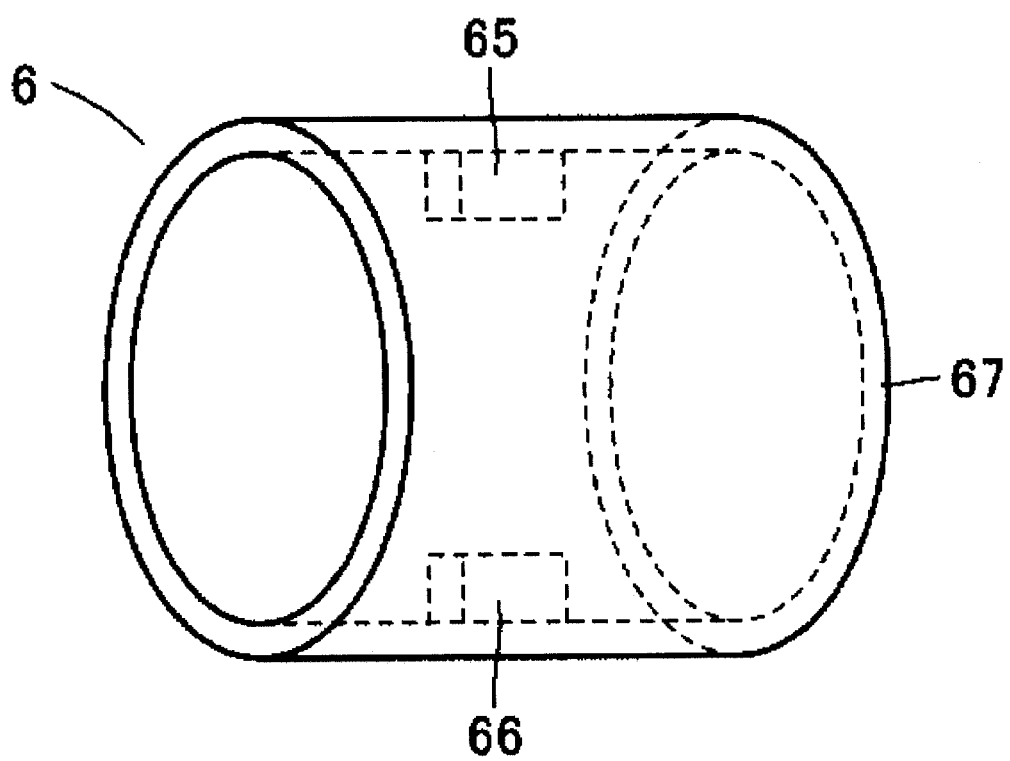
FIG. 3 is a diagram showing an outline of a configuration of a finger cuff.
Figure 4:
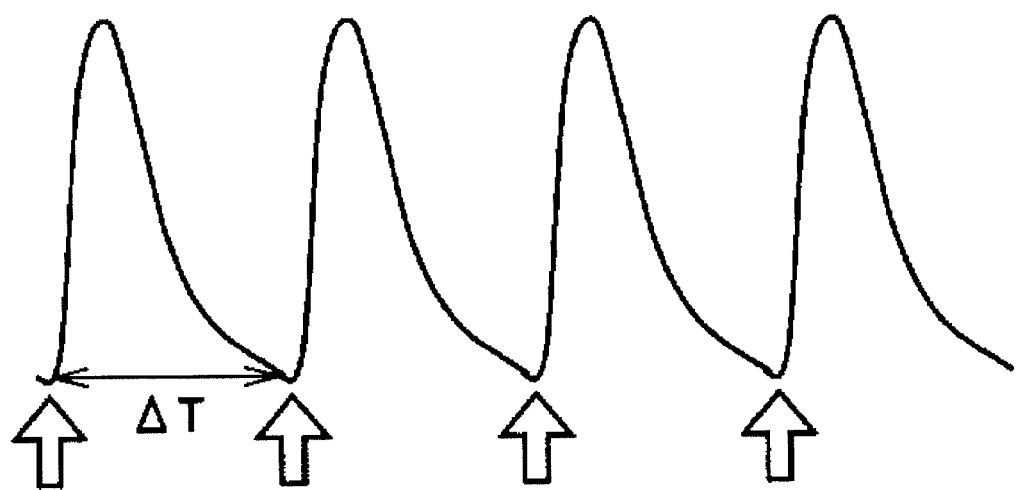
FIG. 4 is a diagram showing a specific example of a pulse wave signal.

Various configurations and structures can be applied to the sensor for detecting the oxygen saturation level in the blood, which is one type of continuous physiological information excluding the blood pressure, in the blood pressure measurement device 1A, but in this case, the finger cuff 6 shown in FIG. 3 is used. The finger cuff 6 is configured to include a cylindrical cuff 67, as well as a light emitting element 65 and a light receiving element 66 incorporated in the cuff 67. In a state where the finger cuff 5 is attached to the finger of the subject, when the light emitting element 65 irradiates the finger with a light ray such as a near-infrared ray, the light ray that transmitted through the finger of the subject is detected by the light receiving element 66. The arterial capacity of the finger portion repeatedly increases or decreases according to the pulsation of the blood pressure, where an amount (intensity) that transmits through the finger of the near-infrared ray that can be easily absorbed to the hemoglobin in the blood changes according to the change in the arterial capacity. The light receiving element 66 outputs the change in the light receiving amount of the near-infrared ray that transmitted through the finger to the pulse wave detecting portion 13 as a signal of a voltage change, or the like. This signal is referred to as a pulse wave signal, and is as shown in FIG. 4. The pulse wave detecting portion 13 detects, as a pulse wave signal, the change in the amount of light transmitted through the finger and received by the light receiving element 66 by clipping a fingertip with the finger cuff 6, and irradiating the finger with two types of light rays having different wavelengths from the light emitting element 65.

The oxygen saturation level calculating portion 14A calculates the oxygen saturation level BI in the blood based on the pulse wave signal detected by the pulse wave detecting portion 13. The calculation method is not limited to a specific method in the present invention, and a method of calculating according to the known procedures is adopted. The calculated oxygen saturation level BI is sequentially inputted to the comparing and determining portion 15. The finger cuff 6, the pulse wave detecting portion 13, and the oxygen saturation level calculating portion 14A configure a detection system of continuous physiological information.

Figure 5:
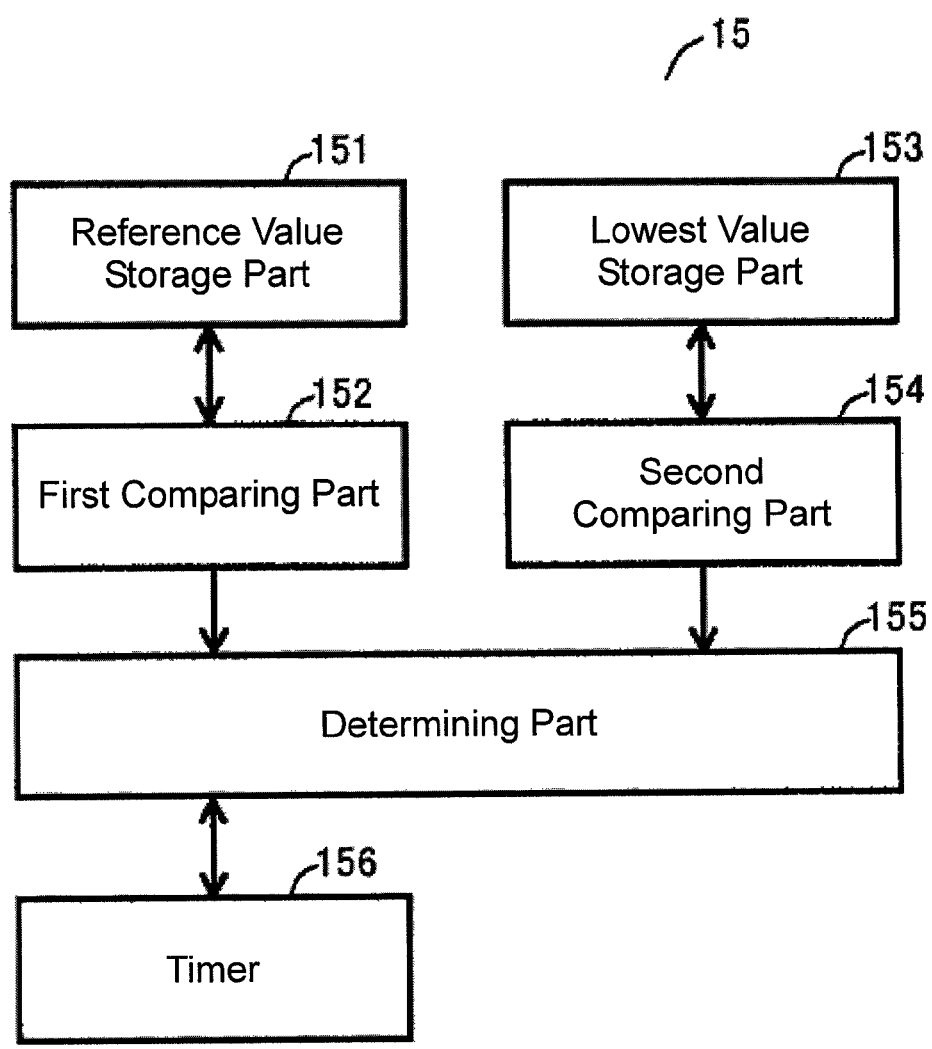
FIG. 5 is a block diagram showing a specific example of a configuration of a comparing and determining portion.

As shown in FIG. 5, the comparing and determining portion 15 includes a reference value storage part 151 for storing a reference value Th in advance, a first comparing part 152 for performing a first comparison using the reference value Th, a lowest value storage part 153 for storing a lowest value BIw of the oxygen saturation level, a second comparing part 154 for performing a second comparison using the lowest value BIw, a determining part 155 for determining whether or not to start the blood pressure measurement, and a timer 156 for timing a time limit that limits the start of the blood pressure measurement.

The reference value storage part 151 stores the reference value Th for determining whether or not to activate in advance. The reference value Th is not limited to a specific value, but is preferably about 90%. The first comparing part 152 sequentially compares the calculated oxygen saturation level BI and the reference value Th, and outputs the comparison result to the determining part 155.

The lowest value storage part 153 stores the lowest value BIw of the oxygen saturation level. The second comparing part 154 sequentially compares the calculated oxygen saturation level BI and the lowest value BIw, and outputs the comparison result to the determining part 155. If the calculated oxygen saturation level BI is smaller than the lowest value BIw stored in the lowest value storage part 153 as a result of comparison, the lowest value BIw stored in the lowest value storage part 153 is updated to the oxygen saturation level BI.

The determining part 155 performs the next determination based on the comparison result from the first comparing part 152 and the second comparing part 154. When the comparison result, where the calculated oxygen saturation level BI is smaller than the reference value Th, is inputted from the first comparing part 152, the determining part 155 determines whether or not the timer 156 is in timing operation and within the time limit. As a result, if detected that the first condition in which the oxygen saturation level BI is smaller than the reference value Th is satisfied when not within the time limit, the determining part 155 determines the start of the blood pressure measurement, and outputs an activation signal instructing the start of the blood pressure measurement with respect to the sphygmomanometer 8. A timing start signal for timing a predetermined time set in advance as a time limit from the end of the blood pressure measurement is outputted to the timer 156. Accordingly, the period of the predetermined time from the end of the blood pressure measurement becomes the time limit in which the start of the blood pressure measurement is limited. Note that the predetermined time is not particularly limited to a specific time in the present invention, and may be 10 minutes or the like.

If the timer 156 is in timing operation when the comparison result that the calculated oxygen saturation level BI is smaller than the reference value Th is inputted from the first comparing part 152, the determining part 155 determines not to activate the blood pressure measurement since it is within the time limit, and does not output the activation signal to the sphygmomanometer 8 at this time. That is, determination is made to not activate the blood pressure measurement even if it is detected that the first condition is satisfied within the time limit.

When the comparison result that the calculated oxygen saturation level BI is greater than the reference value Th is inputted from the first comparing part 152, the determining part 155 determines not to activate the blood pressure measurement since the first condition is not satisfied, and does not output the activation signal to the sphygmomanometer 8.

When the comparison result that the calculated oxygen saturation level BI is smaller than the lowest value BIw stored in the lowest value storage part 153 is inputted from the second comparing part 154, the determining part 155 determines whether or not the timer 156 is in timing operation and is within the time limit. As a result, if the timer 156 is in timing operation, and if the second condition in which the oxygen saturation level BI is smaller than the lowest value BIw is satisfied within the timing limit, the start of the blood pressure measurement is determined, and an activation signal instructing the start of the blood pressure measurement is outputted to the sphygmomanometer 8.

If the timer 156 is not in timing operation when the comparison result that the calculated oxygen saturation level BI is smaller than the lowest value BIw stored in the lowest value storage part 153 is inputted from the second comparing part 154, the determining part 155 determines not to activate the blood pressure measurement, and does not output the activation signal to the sphygmomanometer 8. That is, determination is made not to activate the blood pressure measurement even if detected that the second condition is satisfied when not within the time limit.

When the comparison result that the calculated oxygen saturation level BI is greater than the lowest value BIw stored in the lowest value storage part 153 is inputted from the second comparing part 154, the determining part 155 determines not to activate the blood pressure measurement since the second condition is not satisfied, and does not output the activation signal to the sphygmomanometer 8.

Figure 6:
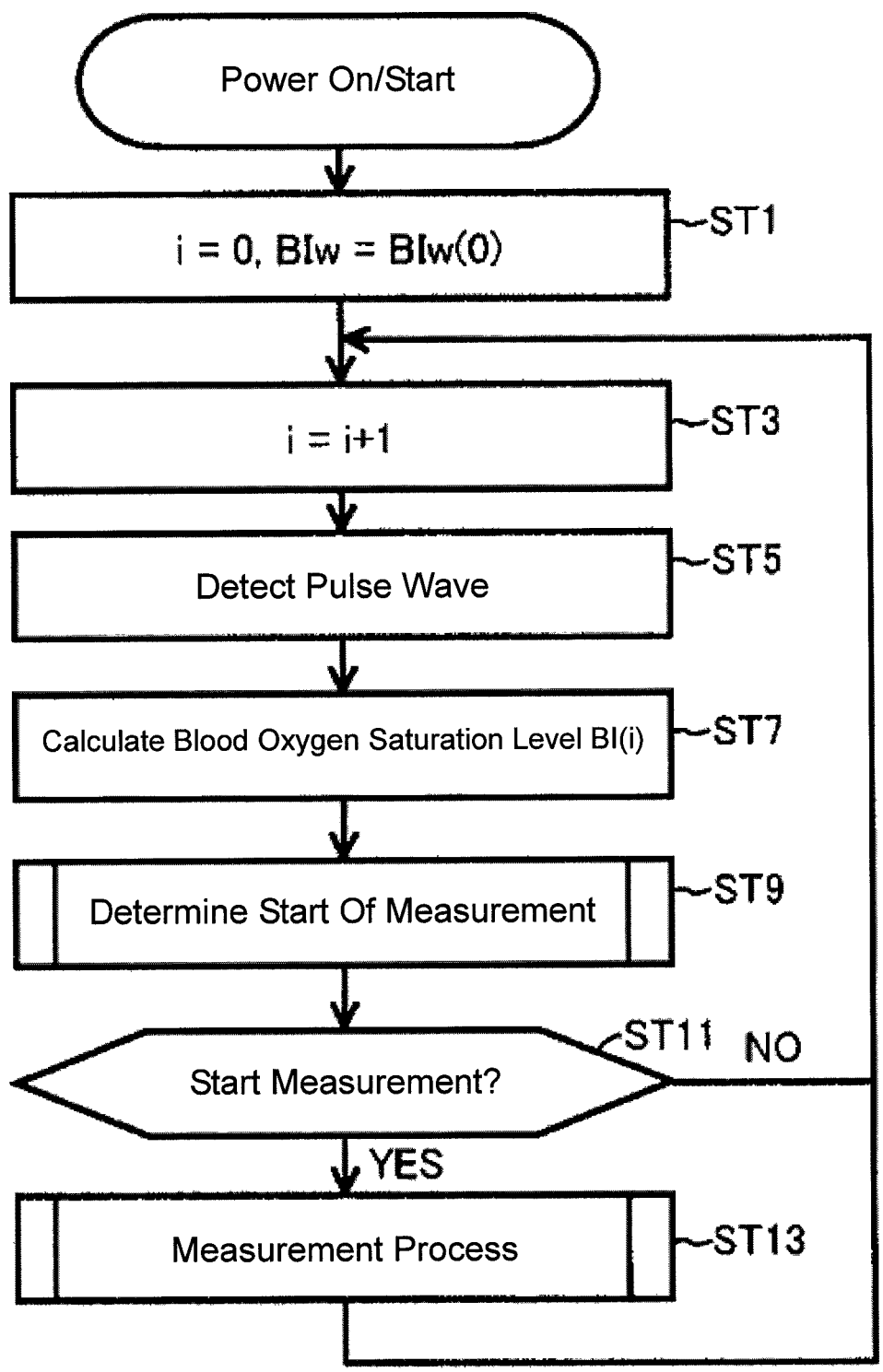
FIG. 6 is a flowchart showing a specific example of a process in the blood pressure measurement device according to the first embodiment.

FIG. 6 is a flowchart showing a specific example of the process for starting the blood pressure measurement in the blood pressure measurement device 1A. The process shown in the flowchart of FIG. 6 is a process started by pushing the power switch 41 to turn ON the power of the blood pressure measurement device 1A, and pushing the measurement start switch 42, and is realized by having the CPU 7 execute the program stored in the memory (not shown) and control each part shown in FIGS. 2 and 5.

With reference to FIG. 6, an initial value 0 of a variable i is first set, and a predetermined initial value BIw(0) is set as the lowest value BIw that is a variable to be stored in the lowest value storage part 153 (step ST1). The initial value BIw(0) is not limited to a specific value and may be an optimum value of the oxygen saturation level or a value same as the reference value Th stored in the reference value storage part 151 as long as it is a known value.

After the variable i is incremented in step ST3, the pulse wave is detected in the pulse wave detecting portion (step ST5), and the oxygen saturation level BI(i) in the blood is calculated based on the pulse wave signal detected in step ST5 in the oxygen saturation level calculating portion 14A (step ST7). The process of determining whether or not to start the blood pressure measurement is performed in the comparing and determining portion 15 using the oxygen saturation level BI(i) calculated in step ST7, the reference value Th, and the lowest value BIw stored in the lowest value storage part 153 (step ST9). If the determination result of step ST9 is "start blood pressure measurement" (YES in step ST11, the blood pressure measurement is executed in step ST13 and the process of obtaining the measurement value is performed, and if the determination result in step ST9 is not "start blood pressure measurement" (NO in step ST11), the process of step ST13 is skipped and the process returns to step ST3.

After returning to step ST3, the above-described processes are repeated until detecting that the power switch 41 is pushed again to turn OFF the power of the blood pressure measurement device 1A, the measurement stop button (not shown) is pushed, or the like.

If the blood pressure measurement device 1A is conducting the blood pressure measurement, even if determined to start the measurement in the determination of step ST9 (YES in step ST11), such determination to start the measurement is canceled, and the determination is not started in step ST13 according to the determination of step ST9.

Figure 7:
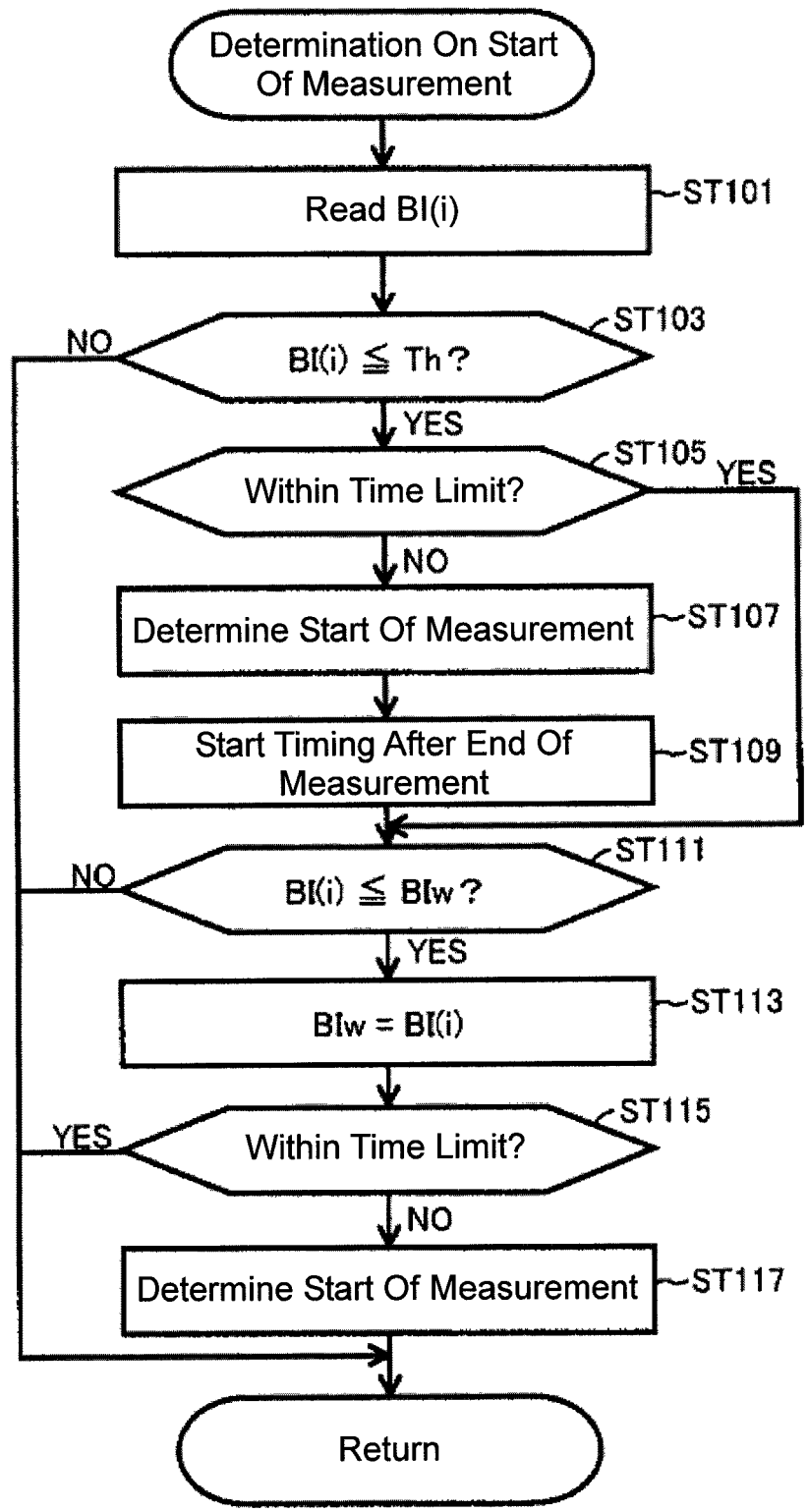
FIG. 7 is a flowchart showing a specific example of a measurement start determination process.

A specific example of the measurement start determination process in step ST9 is shown in FIG. 7.

With reference to FIG. 7, the oxygen saturation level BI(i) calculated in step ST7 corresponding to the set variable i is first read (step ST101) in the first comparing part 152 and the second comparing part 154, and compared with the reference value Th in the first comparing part 152 (step ST103). If the oxygen saturation level BI(i) is smaller than or equal to the reference value Th (YES in step ST103) as a result, the determining part 155 checks whether or not the timer 156 is in timing operation to determine whether or not within the time limit (step ST105). If determined as not within the time limit when the oxygen saturation level BI(i) is smaller than or equal to the reference value Th (YES in step ST103, NO in ST105), the determining part 155 determines to start the measurement (step ST107), and returns the determination result thereof. Furthermore, the process of outputting a control signal for starting the timing in the timer 156 to the timer 156 is performed after the end of measurement (step ST109). If determined as within the time limit (YES in step ST105), steps ST107 and ST109 are skipped, and the determining part 155 does not determine to start the measurement.

The oxygen saturation level BI(i) and the lowest value BIw stored in the lowest value storage part 153 at the time are compared in the second comparing part 154 (step ST111). If the oxygen saturation level BI(i) is smaller than or equal to the lowest value BIw stored in the lowest value storage part 153 at the time as a result (YES in step ST111), the second comparing part 154 updates the lowest value BIw stored in the lowest value storage part 153 to the oxygen saturation level BI(i) at the time (step ST113). The determining part 155 also determines whether or not within the time limit by checking whether or not the timer 156 is in timing operation (step ST115), where the determining part 155 determines to start the measurement (step ST117) and returns the determination result thereof if determined as within the time limit (YES in step ST115) when the oxygen saturation level BI(i) is smaller than or equal to the lowest value BIw. If determined as not within the time limit (NO in step ST115), step ST117 is skipped, and the determining part 155 does not determine to start the measurement.

Figure 8:
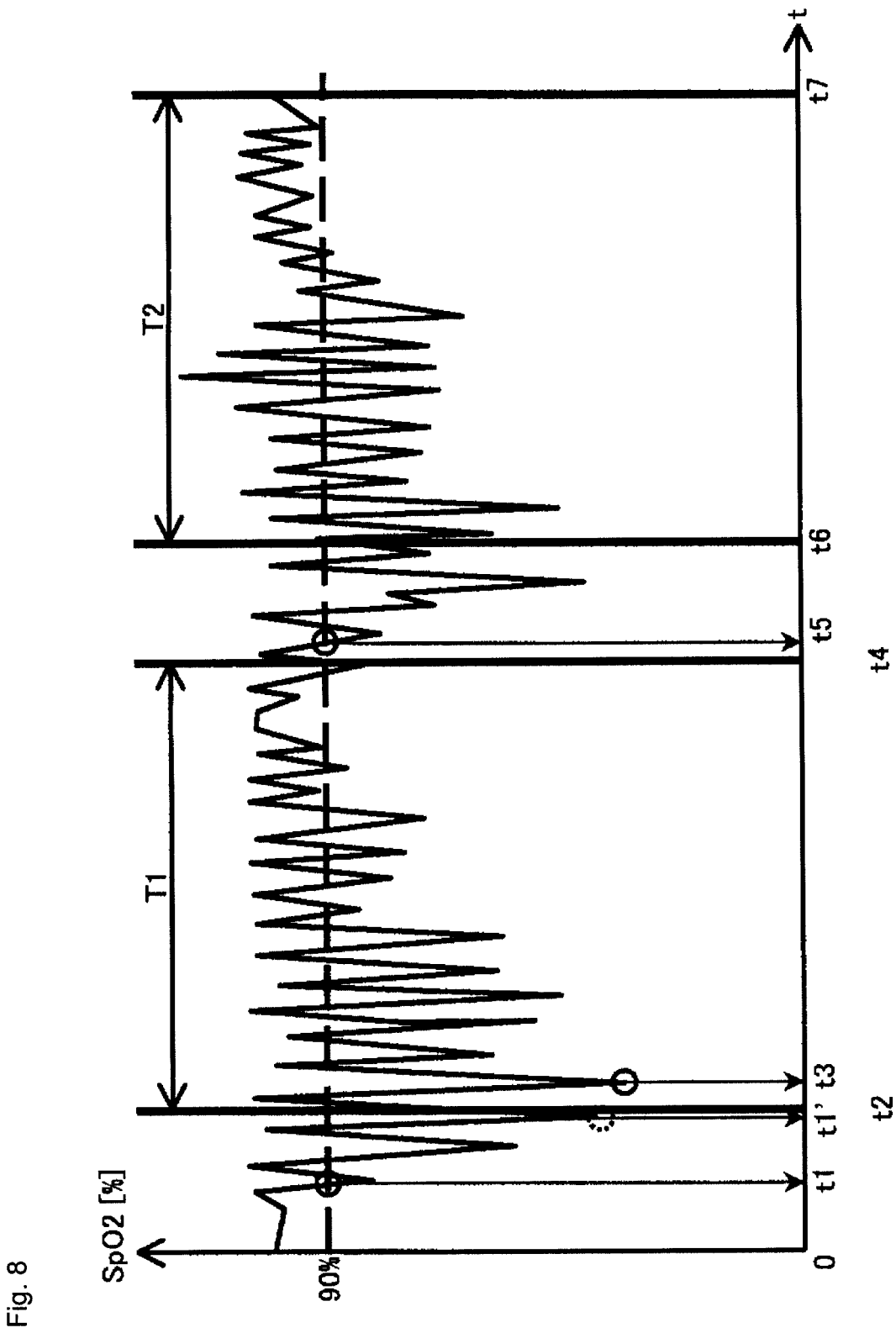
FIG. 8 is a diagram describing a method of determining a start of measurement in the blood pressure measurement device according to the first embodiment.

The above measurement start determination will be described using transition of a specific oxygen saturation level of FIG. 8. FIG. 8 is a diagram showing a specific example of a temporal change in the blood oxygen saturation level (SpO2) from when the process for starting the measurement in the blood pressure measurement device 1A is started, where the temporal change in the blood oxygen saturation level (SpO2) during sleep is shown. The reference value Th herein is indicated as 90%.

With reference to FIG. 8, detection is made that the oxygen saturation level BI is smaller than or equal to the reference value Th for the first time at time t1 since the process started. The start of blood pressure measurement is then determined in step ST107, and the blood pressure measurement process is started. The count of a predetermined time T set in advance is started from time t2 at when the blood pressure measurement ends by step ST109, where the time limit T1 from time t2 to t4 starts.

The lowest value BIw stored in the lowest value storage part 153 is sequentially updated by executing the processes of steps ST111 to ST117, and the oxygen saturation level obtained at time t1' is stored as the lowest value BIw at the time point of time t2 at when the time limit T1 starts.

When the time limit T1 starts, detection is made that the oxygen saturation level BI is smaller than or equal to the lowest value BIw stored in the lowest value storage part 153 at time t3. The start of blood pressure measurement is then determined in step ST117, and the blood pressure measurement process is started. After the blood pressure measurement ends, the start of measurement is not determined even if detected that the oxygen saturation level BI is smaller than or equal to the reference value Th.

When the time limit T1 ends at time t4, detection is made that the oxygen saturation level BI is smaller than or equal to the reference value Th for the first time at time t5 after time t4. The start of blood pressure measurement is then determined in step ST107, and the blood pressure measurement process is started. The count of a predetermined time T set in advance is started from time t6 at when the blood pressure measurement ends by step ST109, where the time limit T2 from time t6 to t7 starts.

As such a determination process is executed in the blood pressure measurement device 1A, the start of measurement is not determined even if detected that the oxygen saturation level BI is smaller than or equal to the reference value Th within the time limit which is a predetermined time after the end of measurement, and the start of the blood pressure measurement process of when the first condition is satisfied is limited. Thus, even when the oxygen saturation level BI of the subject transitions up and down little by little with the reference value Th in between, as shown in FIG. 8, the blood pressure measurement is not frequently performed according to such a transition, and the start of the next blood pressure measurement is limited until a predetermined time has elapsed after the first blood pressure measurement is performed. The physical pain and the psychological pain of the subject thus can be alleviated. Further, the sleep of the subject is suppressed from being inhibited.

With the execution of the above determination process, the start of measurement is determined and the blood pressure measurement is performed when the second condition, i.e. condition by relationship with the lowest value BIw, is satisfied even if within the time limit. Specifically, when the oxygen saturation level BI becomes the lowest from the start of process, the blood pressure measurement is performed even if within the time limit. Thus, the blood pressure measurement can be performed without missing a case where a critical physiologic change such as respiratory arrest including sleep apnea or infrequent respiration occurs or a case where such a physiologic change may occur.

Second Embodiment

A blood pressure measurement device 1B according to a second embodiment determines a measurement start timing based on a change in heart rate, which is one type of continuous physiological information excluding a blood pressure, and starts the measurement.

Having the heart rate as an index to look for the blood pressure measurement start timing has the following significance. That is, the heart rate is an index of sympathetic nerve system activation level, which increase is related to cardiovascular event risk. As the sympathetic nerve system also fluctuates when the heart rate fluctuates, a new blood pressure index leading to the prediction of cardiovascular risk can be obtained by specifying and measuring the blood pressure level. The second embodiment is based on the heart rate, but can be replaced with a pulse rate corresponding to similar physiological phenomenon. In this case, the configuration of the device is similar to the device configuration of the blood pressure measurement device 1A.

The blood pressure measurement device 1B can detect the heart rate using the finger cuff 6 arranged in the blood pressure measurement device 1A, and the outer appearance of the blood pressure measurement device 1B is similar to the outer appearance of the blood pressure measurement device 1A shown in FIG. 1.

Figure 9:
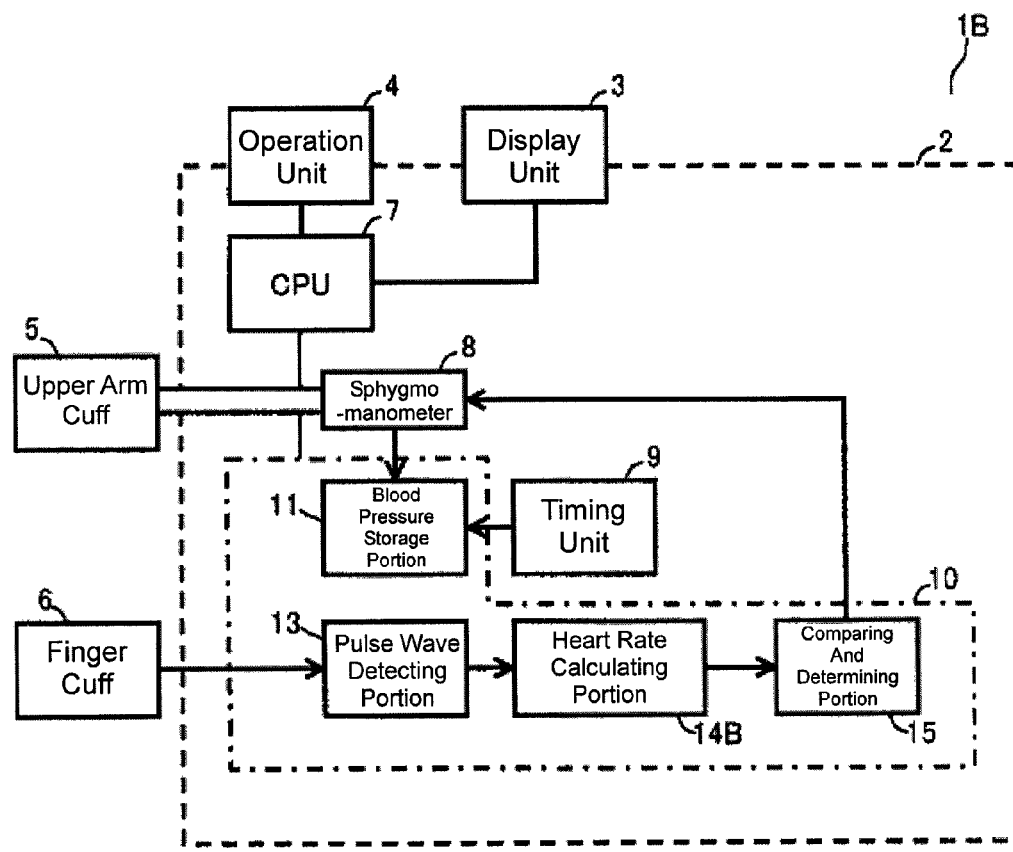
FIG. 9 is a block diagram showing a specific example of a configuration of the blood pressure measurement device according to a second embodiment.

FIG. 9 is a block diagram showing a specific example of the configuration of the blood pressure measurement device 1B. With reference to FIG. 9, the processing unit 10 of the blood pressure measurement device 1B includes a heart rate calculating portion 14B in place of the oxygen saturation level calculating portion 14A, compared with the blood pressure measurement device 1A shown in FIG. 2.

The light receiving element 66 (see FIG. 3) included in the finger cuff 6 outputs the above-mentioned pulse wave signal as shown in FIG. 4 to the pulse wave detecting portion 13. The pulse wave detecting portion 13 receiving the pulse wave signal recognizes the rising point (arrow portion of FIG. 4) of the pulse wave indicated with the pulse wave signal for every beat, and detects the pulse wave. Thereafter, the heart rate calculating portion 14B measures the time interval $\Delta T$ of the rising points of the adjacent pulse waves, and calculates the number of pulses per unit time, that is, the heart rate represented with the pulse rate.

The comparing and determining portion 15 has a configuration substantially the same as the configuration shown in FIG. 5, and includes a storage part for storing a highest value in place of the lowest value storage part 153 with respect to the characteristics of using the heart rate as continuous physiological information.

The process for starting the blood pressure measurement in the blood pressure measurement device 2B and the measurement start determination process are similar to the processes shown in FIGS. 6 and 7. Due to the characteristics of using the heart rate for the continuous physiological information in place of the blood oxygen saturation concentration, the fact that the calculated heart rate is greater than the reference value is used as the first condition, and the fact that the calculated heart rate is greater than the highest value up to the relevant point is used as the second condition.

Figure 10:
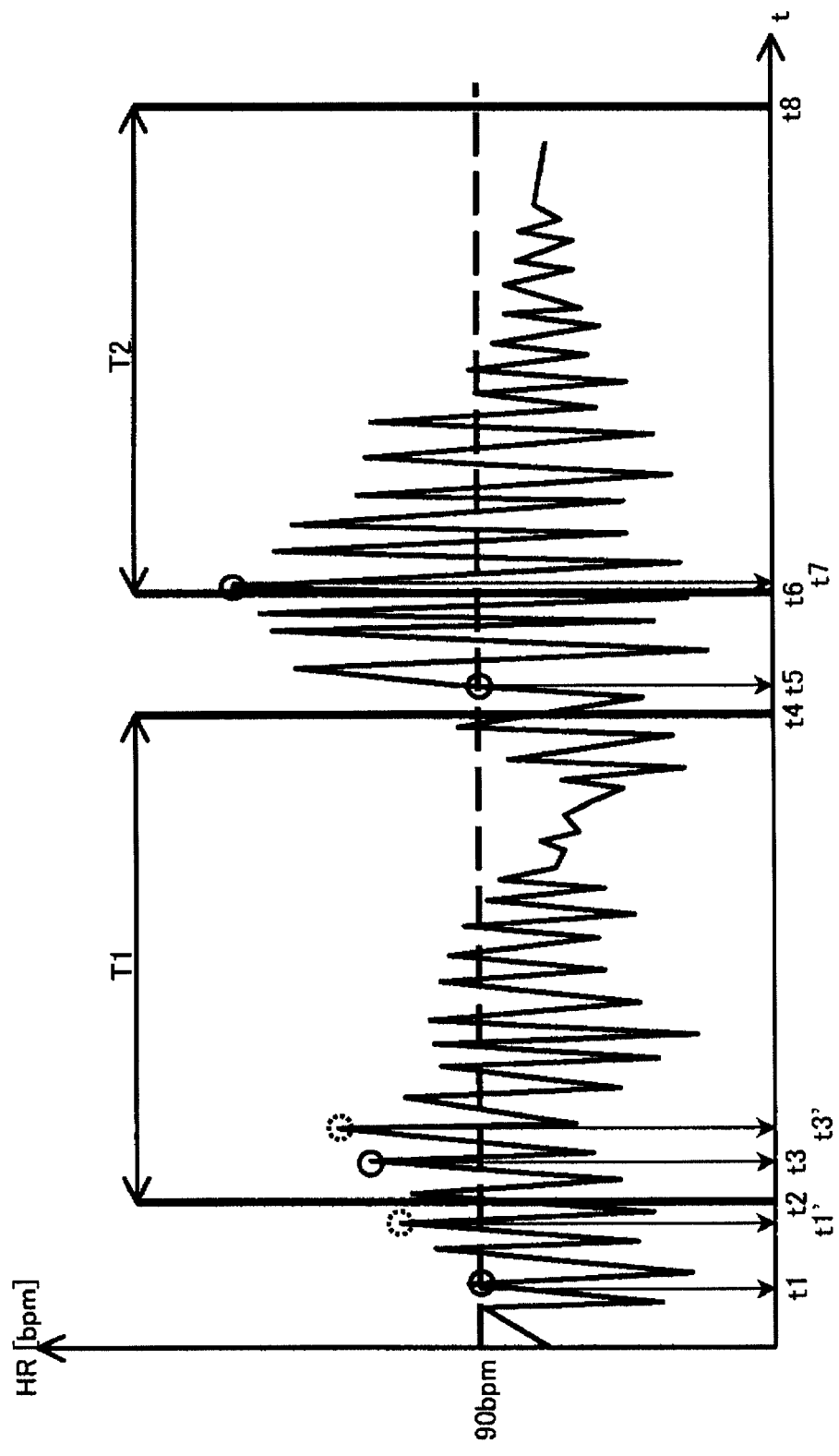
FIG. 10 is a diagram describing a method of determining a start of measurement in the blood pressure measurement device according to the second embodiment.

The measurement start determination in the blood pressure measurement device 1B will be described using a specific transition of the heart rate of FIG. 10. FIG. 10 is a diagram showing a specific example of a temporal change in the heart rate (HR) from when the process of starting the measurement in the blood pressure measurement device 1B is started, where the temporal change in the heart rate (HR) during sleep is shown. The reference value Th herein is specifically indicated as 90 bpm.

With reference to FIG. 10, detection is made that the heart rate is greater than or equal to the reference value Th for the first time at time t1 since the process started. The start of blood pressure measurement is then determined in step ST107, and the blood pressure measurement process is started. The count of a predetermined time T set in advance is started from time t2 at when the blood pressure measurement ends by step ST109, where the time limit T1 from time t2 to t4 starts.

The highest value to be stored is sequentially updated by executing the processes of steps ST111 to ST117, and the heart rate obtained at time t1' is stored as the highest value at the time point of time t2 at when the time limit T1 starts.

When the time limit T1 starts, detection is made that the heart rate is greater than or equal to the highest value at time t3. The start of blood pressure measurement is then determined in step ST117, and the blood pressure measurement process is started. After the blood pressure measurement ends, the start of measurement is not determined even if detected that the heart rate is greater than or equal to the reference value Th. Similarly, detection is made that the heart rate is greater than or equal to the highest value at time t3', and determination is made to start the blood pressure measurement in step ST117, but such determination is canceled and the blood pressure measurement is not started if the blood pressure measurement is already being performed, and thus the blood pressure measurement is not started at time t3' and only the update of the highest value is performed.

When the time limit T1 ends at time t4, detection is made that the heart rate is greater than or equal to the reference value Th for the first time at time t5 after time t4. The start of blood pressure measurement is then determined in step ST107, and the blood pressure measurement process is started. The count of a predetermined time T set in advance is started from time t6 at when the blood pressure measurement ends by step ST109, where the time limit T2 from time t6 to t7 starts.

When the time limit T2 starts, detection is made that the heart rate is greater than or equal to the highest value at time t7, and similarly, the blood pressure measurement process is started.

As such a determination process is executed in the blood pressure measurement device 1B, the start of measurement is not determined even if detected that the heart rate is greater than or equal to the reference value Th within the time limit which is a predetermined time after the end of measurement, and the start of the blood pressure measurement process of when the first condition is satisfied is limited. Thus, even when the heart rate of the subject transitions up and down with the reference value Th in between, as shown in FIG. 10, the blood pressure measurement is not frequently performed according to such a transition, and the start of the next blood pressure measurement is limited until a predetermined time has elapsed after the first blood pressure measurement is performed. The physical pain and the psychological pain of the subject thus can be alleviated. Further, the sleep of the subject is suppressed from being inhibited.

With the execution of the above determination process, the start of measurement is determined and the blood pressure measurement is performed when the second condition, i.e. condition by relationship with the highest value, is satisfied even if within the time limit. Specifically, when the heart rate becomes the highest from the start of process, the blood pressure measurement is performed even if within the time limit. Thus, the blood pressure measurement can be performed without missing a case where a critical physiologic change such as respiratory arrest including sleep apnea or infrequent respiration occurs or a case where such a physiologic change may occur.

Third Embodiment

A blood pressure measurement device 1C according to a third embodiment determines the measurement start timing based on the change in the breathing waveform, which is one type of continuous physiological information excluding a blood pressure, and starts the measurement. Since the breathing waveform is detected by detecting the movement of the chest of the subject with a sensor, for example, the respiratory arrest such as sleep apnea or the infrequent respiration of the subject can be detected by detecting the features of the breathing waveform. As the blood pressure level rapidly rises after the apnea attack, the significance of determining the measurement start timing based on the change in the breathing waveform is to obtain a new blood pressure index leading to the prediction of the cardiovascular risk by specifying and measuring the blood pressure level at the relevant point.

Figure 11:
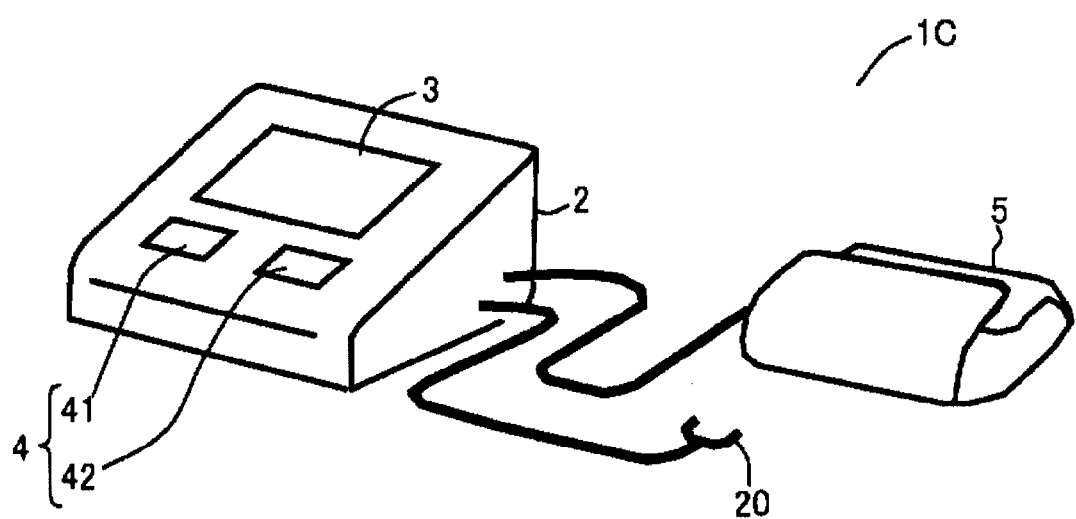
FIG. 11 is a diagram showing a specific example of an outer appearance of a blood pressure measurement device according to a third embodiment.

With reference to FIG. 11, the blood pressure measurement device 1C includes a sensor 20 for detecting the breathing waveform in place of the finger cuff 6, compared to the blood pressure measurement device 1A shown in FIG. 1. Other configurations are substantially the same as the configuration of the blood pressure measurement device 1A. The sensor 20 has a well-known configuration.

Figure 12:
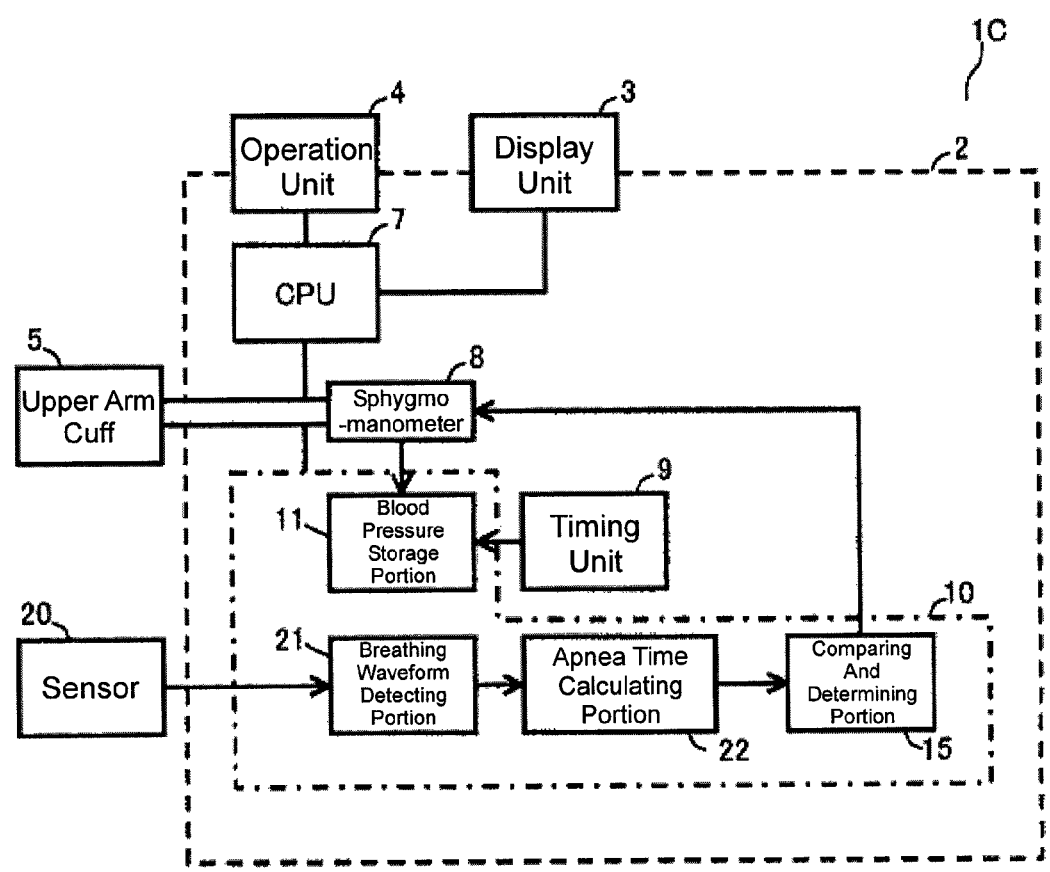
FIG. 12 is a block diagram showing a specific example of a configuration of the blood pressure measurement device according to the third embodiment.

FIG. 12 is a block diagram showing a specific example of a configuration of the blood pressure measurement device 1C. With reference to FIG. 12, the processing unit 10 of the blood pressure measurement device 1C includes a breathing waveform detecting portion 21 and an apnea time calculating portion 22 in place of the pulse wave detecting portion 13 and the oxygen saturation level calculating portion 14A, compared to the blood pressure measurement device 1A shown in FIG. 2.

The sensor 20 monitors the movement of the chest or the stomach of the subject, and outputs an electrical signal based on such movement to the breathing waveform detecting portion 21. The breathing waveform detecting portion 21 detects the change in the electrical signal as a breathing waveform signal. The apnea time calculating portion 22 calculates the apnea time from the breathing waveform detected by the breathing waveform detecting portion 21. Specifically, the apnea time calculating portion 22 stores an upper limit reference value Tu, which is the upper limit of the amplitude of the breathing waveform, and a lower limit reference value Tl, which is the lower limit, starts counting assuming the apnea state or the infrequent respiration state has started from the time point the amplitude of the breathing waveform does not exceed both the upper limit reference value Tu and the lower limit reference value Tl, and performs counting until the time point the amplitude of the breathing waveform exceeds the upper limit reference value Tu or the lower limit reference value Tl. The counted time is outputted to the comparing and determining portion 15 as "apnea time".

The comparing and determining portion 15 has a configuration substantially the same as the configuration shown in FIG. 5, where the reference value storage part 151 stores the reference value Th of the apnea time, and includes a storage part for storing a highest value (longest value) of the apnea time in place of the lowest value storage part 153 due to the characteristics of conditionally using the apnea time as the continuous physiological information. Note that the reference value herein is not limited to a specific value, and five seconds or the like may be used.

The process for starting the blood pressure measurement in the blood pressure measurement device 1C and the measurement start determination process are similar to the processes shown in FIGS. 6 and 7. Due to the characteristics of using the apnea time for the continuous physiological information in place of the blood oxygen saturation concentration, the fact that the calculated apnea time is greater than the reference value is used as the first condition, and the fact that the calculated apnea time is greater than the highest value up to the relevant point is used as the second condition.

Figure 13:
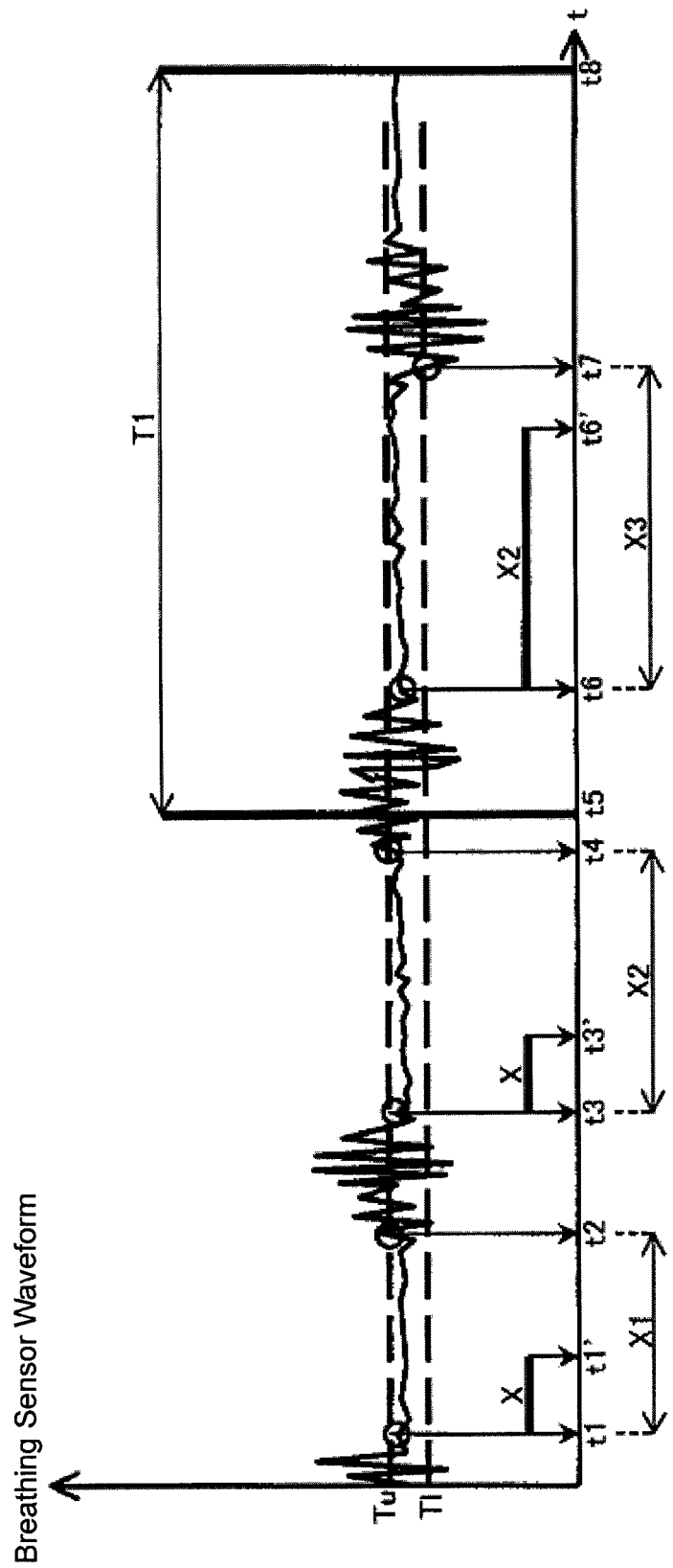
FIG. 13 is a diagram describing a method of determining a start of measurement in the blood pressure measurement device according to the third embodiment.

The measurement start determination in the blood pressure measurement device 1C will be described using a specific transition of the breathing waveform of FIG. 13. FIG. 13 is a diagram showing a specific example of a temporal change in the breathing waveform from when the process of starting the measurement in the blood pressure measurement device 1C is started, where the temporal change in the breathing waveform during sleep is shown.

With reference to FIG. 13, the apnea state is detected for the first time at time t1 since the process is started, and a time X1 up to time t2 is counted as the apnea time in the apnea time calculating portion 22. At time t1', the apnea time is detected as being greater than or equal to time X set as the reference value Th. The start of blood pressure measurement is then determined in step ST107, and the blood pressure measurement process is started. The count of a predetermined time T set in advance is started from time t5 at when the blood pressure measurement ends by step ST109, where the time limit T1 from time t5 to t8 starts.

Similarly, the apnea state is detected at time t3 before time t5, and a time X2 until time t4 is counted as the apnea time in the apnea time calculating portion 22. Similarly, the apnea time is detected as being greater than or equal to time X at time t3', and the start of blood pressure measurement is determined in step ST107, but such determination to start the measurement is canceled as the blood pressure measurement is being carried out.

The highest value of the apnea time to be stored is sequentially updated by executing the processes of ST111 to ST117, and the apnea time X2 counted in the second apnea state is stored as a highest value at the time point of time t5 at when the time limit T1 starts.

After the time limit T1 starts, the apnea state is detected at time t6, and the counting of the apnea time starts. The start of blood pressure measurement is not determined within the time limit T1 even if the counted apnea time reaches the time X. When detected that the counted apnea time is greater than or equal to the time X2, which is the highest value, at time t6', the start of blood pressure measurement is determined in step ST117, and the blood pressure measurement process is started.

As such a determination process is executed in the blood pressure measurement device 1C, the start of measurement is not determined even if detected that the apnea time is greater than or equal to the reference value Th within the time limit which is a predetermined time after the end of measurement, and the start of the blood pressure measurement process of when the first condition is satisfied is limited. Therefore, even if the breathing waveform of the subject is a waveform in which the apnea state is discontinuously repeated, as shown in FIG. 13, the blood pressure measurement is not frequently performed according to such a transition, and the start of the next blood pressure measurement is limited until a predetermined time has elapsed after the first blood pressure measurement is performed. The physical pain and the psychological pain of the subject thus can be alleviated. Further, the sleep of the subject is suppressed from being inhibited.

With the execution of the above determination process, the start of measurement is determined and the blood pressure measurement is performed when the second condition, i.e. condition by relationship with the highest value of the apnea time, is satisfied even if within the time limit. Specifically, when the apnea time becomes the longest from the start of process, the blood pressure measurement is performed even if within the time limit. Thus, the blood pressure measurement can be performed without missing a case where a critical physiologic change such as respiratory arrest including sleep apnea or infrequent respiration occurs or a case where such a physiologic change may occur.

Fourth Embodiment

A blood pressure measurement device 1D according to a fourth embodiment determines a measurement start timing based on a change in cardiograph waveform, which is one type of continuous physiological information excluding a blood pressure, and starts the measurement.

Having the cardiograph waveform as an index to look for the blood pressure measurement start timing has the following significance. That is, the respiratory arrest such as sleep apnea or the infrequent respiration can be detected from the change in the cardiograph waveform. As the blood pressure level rapidly rises after the apnea attack, a new blood pressure index that leads to the prediction of the cardiovascular risk can be obtained by specifying and measuring the blood pressure level at the relevant point.

Figure 14:
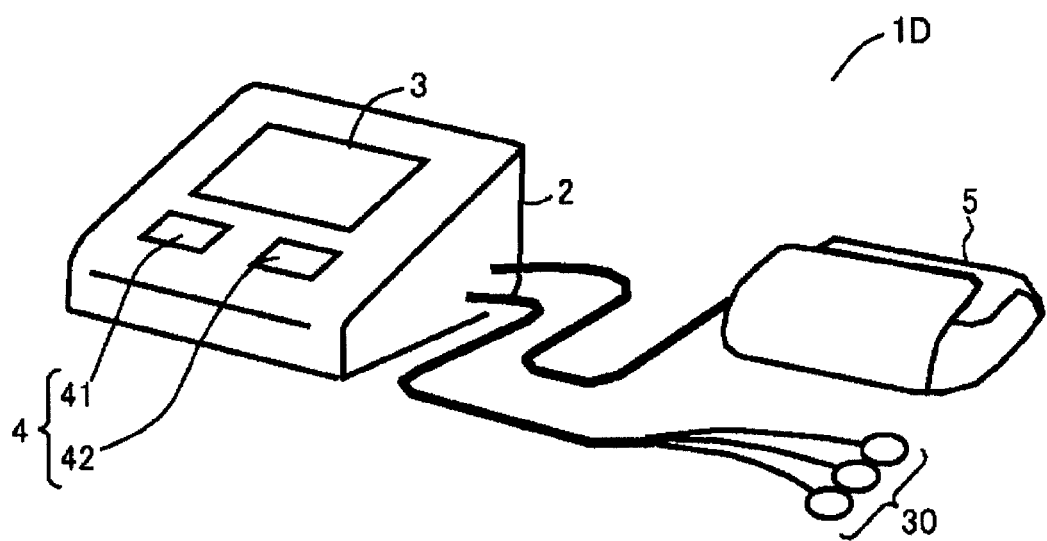
FIG. 14 is a diagram showing a specific example of an outer appearance of a blood pressure measurement device according to a fourth embodiment.

With reference to FIG. 14, the blood pressure measurement device 1D includes a cardiograph sensor 30 in place of the finger cuff 6, compared to the blood pressure measurement device 1A shown in FIG. 1. Other configurations are substantially the same as the configuration of the blood pressure measurement device 1A. The cardiograph sensor 30 has a well-known configuration.

Figure 15:
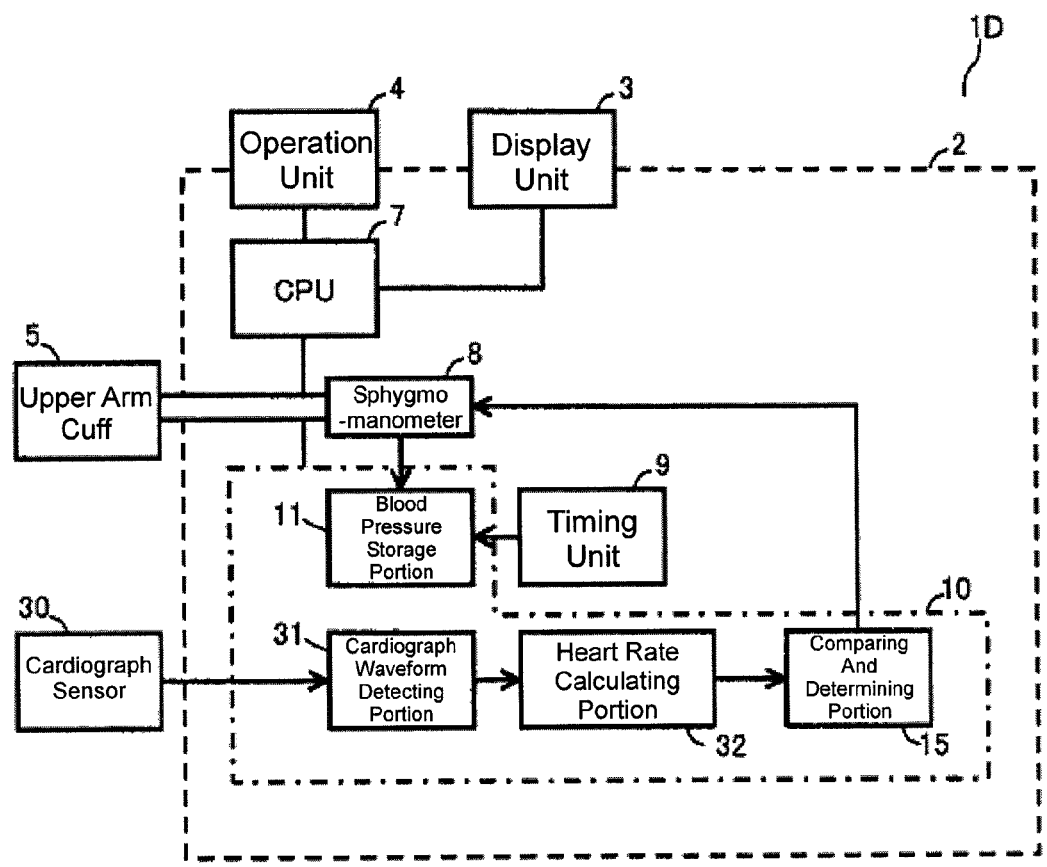
FIG. 15 is a block diagram showing a specific example of a configuration of the blood pressure measurement device according to the fourth embodiment.

FIG. 15 is a block diagram showing a specific example of a configuration of the blood pressure measurement device 1D. With reference to FIG. 15, the processing unit 10 of the blood pressure measurement device 1D includes a cardiograph waveform detecting portion 31 and a heart rate calculating portion 32 in place of the pulse wave detecting portion 13 and the oxygen saturation level calculating portion 14A, compared to the blood pressure measurement device 1A shown in FIG. 2.

The cardiograph sensor 30 includes a plurality of electrodes, and outputs an electrical signal based on a potential difference between at least two sites among the four limbs over the heart to the cardiograph waveform detecting portion 31. The cardiograph waveform detecting portion 31 detects the change in the electrical signal as a cardiograph signal. The heart rate calculating portion 32 calculates the heart rate from the cardiograph waveform detected by the cardiograph waveform detecting portion 31. Specifically, the heart rate calculating portion 32 stores a threshold value Tu, counts a heart beat interval (R-R interval) represented by the time from the time point the amplitude at point R indicating the amplitude of the R wave of the cardiograph waveform exceeds the threshold value Tu to the time point the amplitude exceeds the threshold value Tu the next time, and calculates the heart rate. The calculated heart rate is outputted to the comparing and determining portion 15.

The comparing and determining portion 15 has a configuration substantially the same as the configuration shown in FIG. 5, where the reference value storage part 151 stores the reference value Th of the heart rate, and the lowest value storage part 153 stores the threshold value T1 of the amplitude at a characteristic point in the cardiograph waveform due to the characteristics of conditionally using the cardiograph waveform and the heart rate as the continuous physiological information. The reference value herein is not limited to a specific value, and 90 beats/min or the like may be used. The characteristic point in the cardiograph waveform merely needs to be a point on the cardiograph waveform that characteristically shows a state in which the blood pressure measurement is effective, and is point T corresponding to the T wave in the specific example to obtain the change (so-called ST change) between the S wave indicating the characteristics of the ischemic illness and the T wave, and the change of the T wave (so-called T change).

The process for starting the blood pressure measurement in the blood pressure measurement device 1D and the measurement start determination process are similar to the processes shown in FIGS. 6 and 7. Due to the characteristics of using the cardiograph waveform and the heart rate for the continuous physiological information in place of the blood oxygen saturation concentration, the fact that the calculated heart rate is greater than the reference value Th, that is, the R-R interval is shorter than the defined interval X is used as the first condition, and the fact that the amplitude at point T is smaller than the threshold value T1 is used as the second condition. When determining the start of measurement using the cardiograph waveform and the heart rate, the process of updating the highest value is not performed in ST113, and the threshold value Tu stored in the lowest value storage part 153 is used in the comparison in the second comparing part 154.

Figure 16:
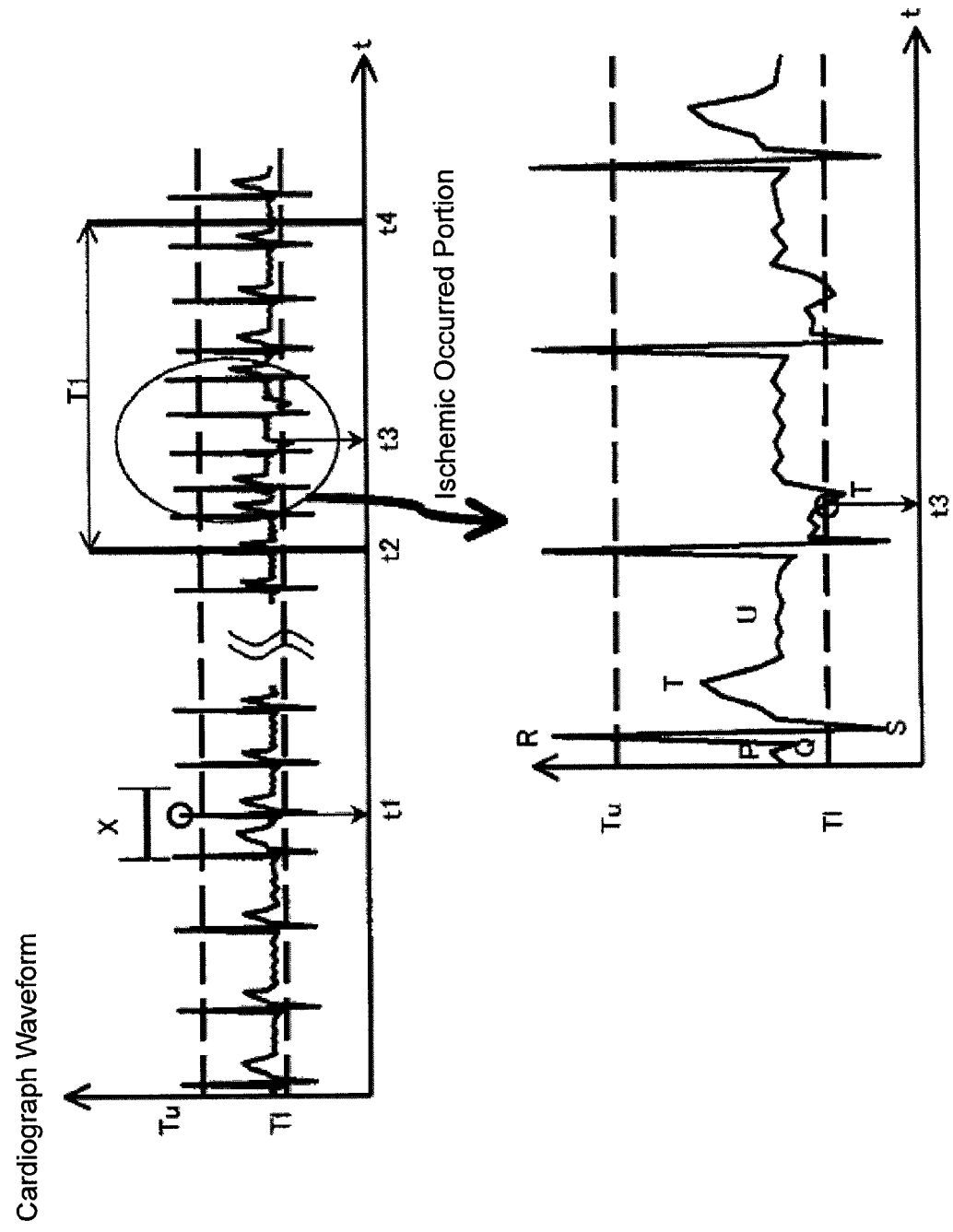
FIG. 16 is a diagram describing a method of determining a start of measurement in the blood pressure measurement device according to the fourth embodiment.

The measurement start determination in the blood pressure measurement device 1D will be described using a specific transition of the breathing waveform of FIG. 16. A portion (A) of FIG. 16 is a diagram showing a specific example of a temporal change in the cardiograph waveform from when the process of starting the measurement in the blood pressure measurement device 1D is started, where the temporal change in the cardiograph waveform during sleep is shown. A portion (B) of FIG. 16 shows, in an enlarged manner, the waveform of one part in the cardiograph waveform shown in the portion (A) of FIG. 16.

With reference to the portion (A) of FIG. 16, when the process is started, the time from point R within the waveform of one beat to point R of the next beat is counted, and the heart rate obtained from such an interval is detected as being greater than the reference value Th, that is the R-R interval is shorter than the defined interval X at time t1. The start of blood pressure measurement is then determined in step ST107, and the blood pressure measurement process is started. The count of a predetermined time T set in advance is started from time t2 at when the blood pressure measurement ends by step ST109, where the time limit T1 from time t2 to t4 starts. One portion of the cardiograph waveform within the time limit T1 is shown in the portion (B) of FIG. 16.

With reference to the portion (B) of FIG. 16, after the time limit T1 starts, whether or not the waveform drops again crossing the threshold value Tu while changing from point S to point T crossing the threshold value Tu within the waveform of one beat is monitored in place of the first condition. When the waveform drops again crossing the threshold value Tu while changing from point S to point T at time t3, and the T wave is detected as being smaller than or equal to the threshold value Tu, the start of blood pressure measurement is determined in step ST117, and the blood pressure measurement process is started.

As such a determination process is executed in the blood pressure measurement device 1D, the start of measurement is not determined even if detected that the heart rate is greater than or equal to the reference value Th within the time limit which is a predetermined time after the end of measurement, and the start of the blood pressure measurement process of when the first condition is satisfied is limited. Therefore, even if the cardiograph waveform of the subject is a waveform in which the increase in heart rate is discontinuously repeated, as shown in FIG. 16, the blood pressure measurement is not frequently performed according to such a transition, and the start of the next blood pressure measurement is limited until a predetermined time has elapsed after the first blood pressure measurement is performed. The physical pain and the psychological pain of the subject thus can be alleviated. Further, the sleep of the subject is suppressed from being inhibited.

Through the above-described determination process, the start of measurement is determined, and the blood pressure measurement is performed even within the time limit if the second condition, i.e. the condition that depends on the relationship between the amplitude at a predetermined characteristic point on the cardiograph waveform and the threshold value, is satisfied. Specifically, the blood pressure measurement is performed if the amplitude at point T becomes smaller than or equal to the threshold value even if within the time limit. Thus, the blood pressure measurement can be performed without missing a case where a critical physiologic change such as an ischemia state occurs or a case where such a physiologic change may occur.

[Variant]

In the above-described embodiments, a value defined in advance is stored in the reference value storage part 151 as the reference value Th used in the first comparing part 152, but may be updated for every predetermined interval during the process based on the obtained continuous physiological information. A specific example of this case will be described in the case of determining the measurement start timing using the blood oxygen saturation level, which is one type of continuous physiological information excluding a blood pressure in the blood pressure measurement device 1A. Needless to say, this is the same in all blood pressure measurement devices 1B to 1D described above.

Figure 17:
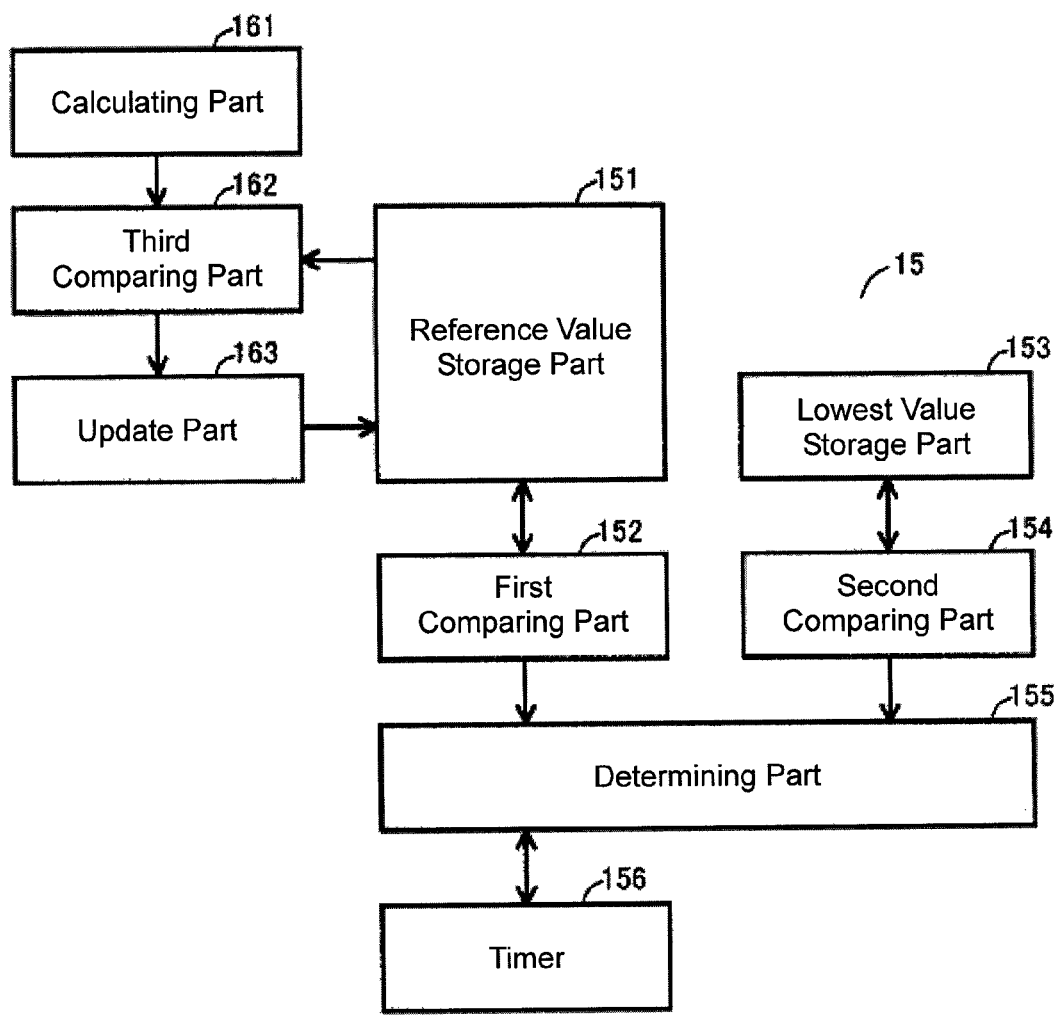
FIG. 17 is a block diagram showing a specific example of a configuration of a comparing and determining portion of a blood pressure measurement device according to a variant.

FIG. 17 is a block diagram showing a specific example of a configuration of a comparing and determining portion 15 of a blood pressure measurement device 1A according to a variant. The comparing and determining portion 15 according to the variant shown in FIG. 17 further includes a calculating part 161, a third comparing part 162, and an update part 163 as a configuration for updating the reference value, in addition to the configuration shown in FIG. 5.

The calculating part 161 calculates a characteristic value using the calculated oxygen saturation level for every predetermined interval during the process of continuously calculating the oxygen saturation level in the blood pressure measurement device 1A, and outputs the characteristic value to the third comparing part 162. The characteristic value is not limited to a specific value, and merely needs to be a value obtained by calculating from the value obtained in the relevant interval. Specifically, the average value, the standard deviation value, and the like of the oxygen saturation levels within the interval may be used.

The third comparing part 162 compares the inputted characteristic value and the reference value Th stored in the reference value storage part 151, and outputs the comparison result to the update part 163. The update part 163 does not update the reference value Th stored in the reference value storage part 151 when the relationship of such values is a predefined relationship, that is, when the inputted characteristic value is within a predetermined range from the reference value Th, and rewrites the reference value Th stored in the reference value storage part 151 to the characteristic value when the relationship is not the predefined relationship, that is, when the inputted characteristic value is outside the predetermined range from the reference value Th.

Figure 18:
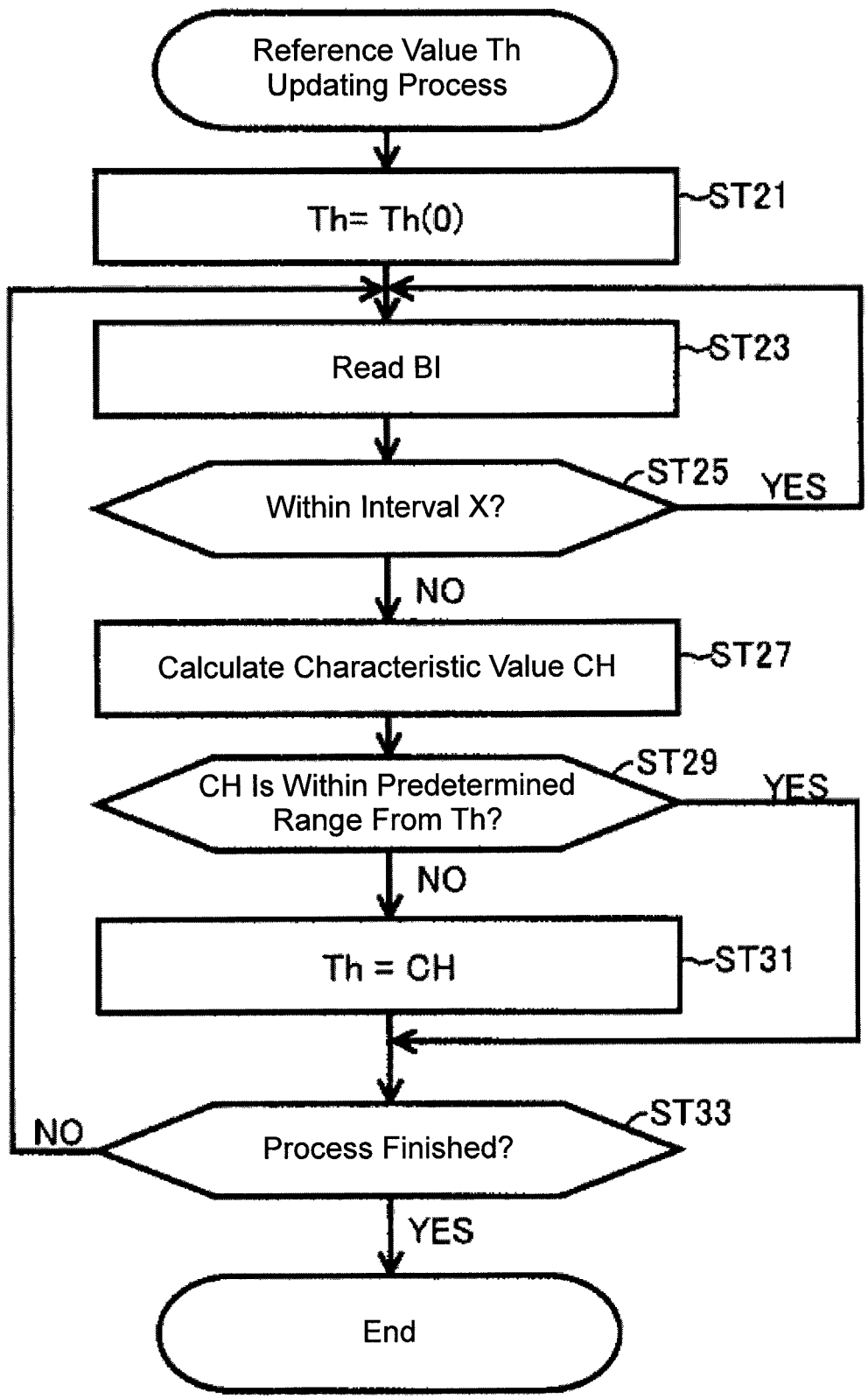
FIG. 18 is a flowchart showing a specific example of a process of updating a reference value.

FIG. 18 is a flowchart showing a specific example of a process of updating the reference value Th performed while the process for starting the blood pressure measurement is being executed in the blood pressure measurement device 1A. The process shown in the flowchart of FIG. 18 is also a process that starts when the power switch 41 is pushed to turn ON the blood pressure measurement device 1A, and the measurement start switch 42 is pushed, and can be implemented when the CPU 7 executes the program stored in the memory (not shown) and controls each part shown in FIGS. 2 and 17.

With reference to FIG. 18, a predetermined initial value Th(0) is first set as the reference value Th stored in the reference value storage part 151 (step ST21).

Then, the calculated oxygen saturation level BI in the predefined interval X is read (steps ST23, ST25), and a characteristic value CH for such an interval is calculated by the calculating part 161 (step ST27). The characteristic value CH of the relevant interval calculated in step ST27 is compared with the reference value Th stored in the reference value storage part 151 by the third comparing part 162 (step ST29), and if the characteristic value CH is not within the predetermined range from the reference value Th (NO in step ST29), the reference value Th is updated by being rewritten to the characteristic value CH of the interval calculated in step ST27 in the update part 163 (step ST31). If not (YES in step ST29), step ST31 is skipped and the reference value Th is not updated.

The processes of the above steps ST23 to ST31 are repeated until the process of starting the blood pressure measurement in the blood pressure measurement device 1A ends, and the reference value Th is updated for every interval.

Figure 19:
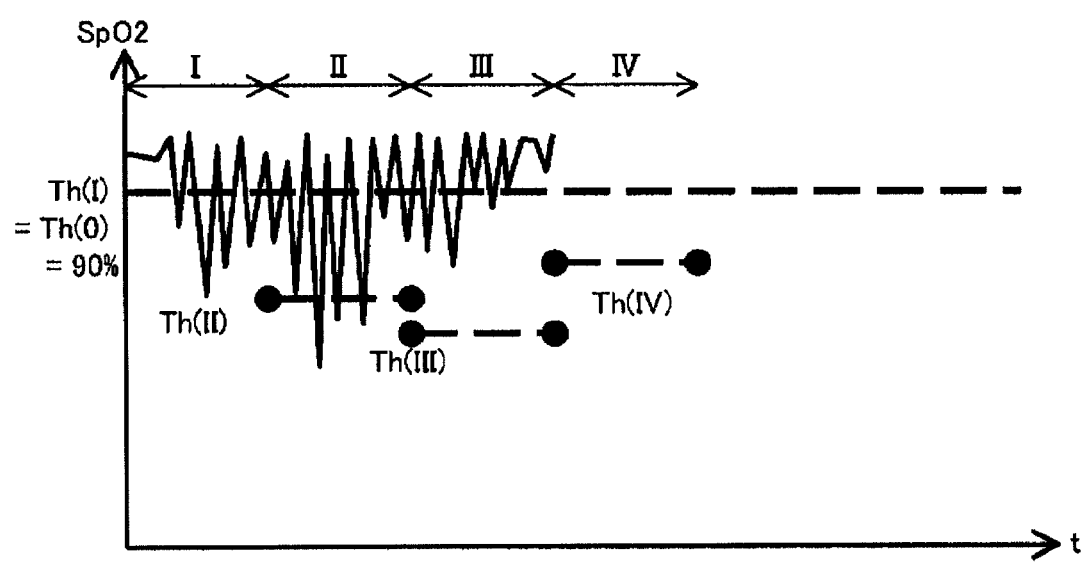
FIG. 19 is a diagram describing a method of updating the reference value.

The above method of updating the reference value will be described using a specific transition of the oxygen saturation level of FIG. 19. FIG. 19 is a diagram showing a specific example of a temporal change of the blood oxygen saturation level (SpO2) from the start of the process for starting the measurement in the blood pressure measurement device 1A.

With reference to FIG. 19, assuming that 90% is set as the initial value of the reference value Th, 90%, which is the initial value, is stored in the reference value storage part 151 as a reference value Th(I) to be used in an interval I, which is a first interval, for continuously calculating the oxygen saturation level.

After the calculation of the oxygen saturation level in the interval I is completed, the characteristic value CH of the interval I is calculated in step ST27, which is then compared with the reference value Th(I) in step ST29. If the characteristic value CH is not within a predetermined range from the reference value Th(I) as a result, the reference value Th(I) stored in the reference value storage part 151 is updated to the characteristic value CH as a reference value Th(II) to be used in an interval II, which is the next interval. As a result, the reference value Th(II) that takes into consideration the characteristics of the oxygen saturation level in the interval I is used for the comparison in the first comparing part 152 in the interval II.

Similarly, in the following intervals III, IV as well, the reference value is updated to the reference value Th that takes into consideration the characteristic of the oxygen saturation level in the previous interval if the characteristic value CH obtained from the oxygen saturation level in the previous interval is not within the predetermined range from the reference value Th used in the previous interval.

Whether or not the first condition is satisfied is determined according to the tendency of the physiological information of the subject by updating the reference value based on the obtained continuous physiological information, and thus the physical pain and the psychological pain of the user caused by the blood pressure measurement can be alleviated. The sleep of the subject is further suppressed from being inhibited.

The physiological information used in the first to the fourth embodiments is a specific example of the continuous physiological information excluding a blood pressure, and thus is not limited to such information, and other information may be used. Other information may be arterial elasticity, pulse wave propagation speed, blood vessel compliance, breathing cycle, breathing frequency, and the like. At least two of such information may be combined to determine the blood pressure measurement start timing.

Further, the process of determining the blood pressure measurement start timing and the process of updating the reference value may be executed by a computer. The computer may be a computer mounted with the blood pressure measurement device 1A to 1D, or may be a computer connected to a device for measuring and calculating the physiological information, the computer determining the blood pressure measurement start timing by executing the above processes based on the physiological information obtained from the device. The latter computer may be connected to the blood pressure measurement device, and output an activation signal to the blood pressure measurement device at a determined timing.

The programs for executing the processes in the computer may be provided as a program product by being recorded in a computer readable recording medium such as a flexible disc, a CD-ROM (Compact Disc-Read Only Memory), a ROM (Read Only Memory), a RAM (Random Access Memory), a memory card, or the like attached to the computer. Alternatively, the program may be provided by being recorded in a recording medium such as a hard disk built in the computer. The program may also be provided by downloading through the network. The present invention encompasses the program itself, the recording medium recorded with the program, and the like.

The program according to the present invention may cause a necessary module of the program modules provided as one part of the operating system (OS) of the computer to be called out in a predetermined array and at a predetermined timing, and execute the process. In this case, the program itself does not include the module, and the process is executed in cooperation with the OS. The program according to the present invention may also include such a program that does not include the module.

The program according to the present invention may be provided by being incorporated in one part of another program. In this case as well, the program itself does not include the module included in another program, and the process is executed in cooperation with another program. The program according to the present invention may also include such a program incorporated in another program.

The provided program product is installed in a program storage unit such as a hard disk, and then executed. The program product includes the program itself and the recording medium recorded with the program.

The embodiments disclosed herein are illustrative in all aspects and should not be construed as being restrictive. The scope of the invention is defined by the claims rather than by the description of the embodiments made above, and all modifications within the meaning and the scope equivalent to the claims are intended to be encompassed.

The invention claimed is:

1. A blood pressure measurement device comprising:
    a sphygmomanometer that measures a blood pressure of a subject;
    a sensor that detects physiological information on a type excluding the blood pressure of the subject; and
    a processor that determines a start of blood pressure measurement in the sphygmomanometer that counts a predetermined time, based on an end of a blood pressure measurement, that limits the start of the blood pressure measurement based on the physiological information, and that outputs a control signal for activating the sphygmomanometer,
    wherein the processor determines a first condition, determines to start the blood pressure measurement when a value obtained from the physiological information satisfies the first condition during a period outside the predetermined time, and determines to start counting the predetermined time from the end of the blood pressure measurement,
    wherein the processor determines not to start the blood pressure measurement during the predetermined time, if the value obtained from the physiological information satisfies the first condition, wherein the processor determines a second condition, determines to start the blood pressure measurement when the value obtained from the physiological information satisfies the second condition during the predetermined time, wherein the second condition is more critically severe than the first condition, and the physiological information of the second condition is of a same type as that of the first condition, and wherein the processor determines not to start the blood pressure measurement during the predetermined time unless the second condition that is more critically severe than the first condition is satisfied.

2. The blood pressure measurement device according to claim 1, wherein the physiological information is a blood oxygen saturation level, wherein the processor comprises:
- a first memory that stores a reference value of the blood saturation level; and
- a second memory that stores a lowest value of the blood saturation level from the start of a determination process in the processor, wherein the first condition is when the blood saturation level becomes smaller than the reference value, and wherein the second condition is when the blood saturation level becomes smaller than the lowest value.

3. The blood pressure measurement device according to claim 1, wherein the physiological information is a heart rate, wherein the processor comprises:
- a first memory that stores a reference value of the heart rate; and
- a second memory that stores a highest value of the heart rate from the start of the determination process in the processor, wherein the first condition is when the heart rate becomes greater than the reference value, and wherein the second condition is when the heart rate becomes greater than the highest value.

4. The blood pressure measurement device according to claim 1, wherein the physiological information is a breathing waveform, wherein the processor detects an apnea or an infrequent respiration state based on the breathing waveform, wherein the processor further comprises:
- a first memory that stores a reference value of a duration of the apnea or the infrequent respiration state; and
- a second memory that stores a longest value of the duration from the start of the determination process in the processor, wherein the first condition is when the duration becomes longer than the reference value, and wherein the second condition is when the duration becomes longer than the longest value.

5. The blood pressure measurement device according to claim 1, wherein the physiological information is a cardiograph waveform, wherein the processor detects a heart rate based on the cardiograph waveform, wherein the processor further comprises:
- a first memory that stores a first reference value of the heart rate; and
- a second memory that stores a second reference value having an amplitude of a T wave of a plurality of waveforms forming the cardiograph waveform of one beat, wherein the first condition is when the heart rate becomes greater than the first reference value, and wherein the second condition is when the amplitude of the T wave becomes smaller than the second reference value.

6. The blood pressure measurement device according to claim 1, wherein the physiological information is at least one of a blood oxygen saturation level, a heart rate, a breathing waveform, and a cardiograph waveform.

7. A blood pressure measurement device comprising:
- a sphygmomanometer that measures a blood pressure of a subject;
- a sensor that detects physiological information on a type excluding the blood pressure of the subject; and
- a processor that determines a first condition when the physiological information enters a first severe level, that determines a start of blood pressure measurement in the sphygmomanometer, and that starts a counting of a predetermined time, during which the start of the blood pressure measurement is limited such that:
  - when the predetermined time counting has not started and when the first condition is detected, the blood pressure measurement starts and, after the blood pressure measurement is completed, the counting of the predetermined time starts; and
  - during the counting of the predetermined time, the blood pressure measurement is limited from being started when the first condition is detected, wherein the processor further determines a second condition when the physiological information enters a second severe level, and determines to start the blood pressure measurement when the second condition is detected during the predetermined time, wherein the second severe level is at a different level than the first severe level, and the physiological information of the second severe level is of a same type as that of the first severe level, and wherein the processor determines to limit the start of the blood pressure measurement during the predetermined time unless the second condition, which is associated with the second severe level at the different level than the first severe level associated with the first condition, is satisfied.

* * * * *